(12) United States Patent
McCluskey et al.

(10) Patent No.: US 9,020,605 B2
(45) Date of Patent: Apr. 28, 2015

(54) ELECTROPORATION DEVICE

(71) Applicant: OncoSec Medical Incorporated, San Diego, CA (US)

(72) Inventors: Brian McCluskey, San Diego, CA (US); Punit Dhillon, San Diego, CA (US)

(73) Assignee: OncoSec Medical Incorporated, San Diego, CA (US)

( * ) Notice: Subject to any disclaimer, the term of this patent is extended or adjusted under 35 U.S.C. 154(b) by 0 days.

(21) Appl. No.: 14/062,582

(22) Filed: Oct. 24, 2013

(65) Prior Publication Data

US 2014/0121728 A1 May 1, 2014

Related U.S. Application Data

(60) Provisional application No. 61/718,561, filed on Oct. 25, 2012, provisional application No. 61/767,078, filed on Feb. 20, 2013, provisional application No. 61/791,968, filed on Mar. 15, 2013.

(51) Int. Cl.
  *A61N 1/00* (2006.01)
  *A61N 1/05* (2006.01)
  *A61N 1/32* (2006.01)
  *A61F 7/00* (2006.01)

(52) U.S. Cl.
  CPC ............... *A61N 1/0502* (2013.01); *A61F 7/007* (2013.01); *A61F 2007/0075* (2013.01); *A61N 1/327* (2013.01)

(58) Field of Classification Search
  None
  See application file for complete search history.

(56) References Cited

U.S. PATENT DOCUMENTS

| 5,036,858 | A | 8/1991 | Carter et al. |
| 6,152,882 | A | 11/2000 | Prutchi |
| 2009/0254019 | A1* | 10/2009 | Gehl et al. .................... 604/21 |
| 2010/0030211 | A1 | 2/2010 | Davalos et al. |
| 2010/0179530 | A1 | 7/2010 | Long et al. |
| 2011/0306943 | A1 | 12/2011 | Dunbar et al. |

FOREIGN PATENT DOCUMENTS

WO   92/01464   2/1992

OTHER PUBLICATIONS

International Search Report and Written Opinion for Application No. PCT/US13/66640 dated Apr. 15, 2014 (19 pages).

* cited by examiner

*Primary Examiner* — Allison Fox
*Assistant Examiner* — Susan E Fernandez
(74) *Attorney, Agent, or Firm* — Michael Best & Friedrich LLP

(57) ABSTRACT

An electroporation device produces electric signals that may be adjusted in response to a cover area of electrodes, so that the electric signals are tolerable when delivered to cells within the cover area. The electroporation device can include an applicator, a plurality of electrodes extending from the applicator, a power supply in electrical communication with the electrodes, and a guide member coupled to the electrodes. The electrodes are associated with a cover area. The power supply is configured to generate one or more electroporating signals to cells within the cover area. The guide member can be configured to adjust the cover area of the electrodes. In some embodiments, the electrical signals may include opposing waveforms that produce a resultant interference waveform to effectively target the cover area, and each waveform may be a unipolar waveform or a bipolar waveform.

19 Claims, 19 Drawing Sheets

ELECTROPORATION DEVICE

CROSS-REFERENCE TO RELATED APPLICATIONS

This claims priority to U.S. Provisional Application No. 61/718,561, filed Oct. 25, 2012, U.S. Provisional Application No. 61/767,078, filed Feb. 20, 2013 and U.S. Provisional Application No. 61/791,968, filed Mar. 15, 2013, the contents of all of which are fully incorporated herein.

TECHNICAL FIELD

This invention relates to an electroporation device configured to deliver one or more electroporating signals in a tolerable manner.

BACKGROUND

In the 1970's, it was discovered that electrical fields could be used to create pores in cells without causing permanent damage to the cell. This discovery made it possible for large molecules, ions, and water to be introduced into a cell's cytoplasm through the cell wall. In some instances, electroporation can be used in topical treatments, such as for head and neck cancer, to introduce chemicals and other compounds into the tumor. During these procedures, the patient may not be under general anesthesia so pain and involuntary muscle movement should preferably be minimized.

Some electroporation devices can produce pulse trains that induce electroporation within a cell's wall to allow the introduction of large molecules, ions, and water into the cell's cytoplasm. However, their electric field or signal frequency (generally about 3.3 Hz) necessary to create the electroporation effect might cause the patient to experience significant pain while receiving treatment. The pain may be at least in part a result of an inverse effect that the frequency or electric field has on skin impedance when an electromagnetic wave is traveling through flesh. For example, skin impedance at 50 Hz is approximately 32000Ω while skin impedance at 4000 Hz is reduced to approximately 40Ω. It has been observed that the higher the impedance, the greater the pain.

Therefore, there is a need in the art for an electoporation device that delivers a strong enough pulse for delivering an agent for treatment, but prevents pain due to cell structure impedance.

SUMMARY

The present invention is directed to an electroporation device comprising an applicator, a plurality of electrodes extending from the applicator, a power supply in electrical communication with the electrodes, and a guide member coupled to the electrodes. The electrodes may be associated with a cover area. The power supply may be configured to generate one or more electroporating signals to cells within the cover area. The guide member may be configured to adjust the cover area of the electrodes. The guide member may be slidably coupled to the applicator.

The guide member may be slidably coupled to the applicator and the applicator may be associated with an applicator end. Sliding the guide member toward the applicator end may decrease the cover area.

The guide member may be slidably coupled to the applicator. The applicator may be associated with an applicator end. Sliding the guide member away from the applicator end may increase the cover area.

At least a portion of the electrodes may be positioned within the applicator in a conical arrangement. The one or more electroporating signals may be each associated with an electric field. The device may further comprise a potentiometer coupled to the power supply and electrodes. The potentiometer may be configured to maintain the electric field substantially within a predetermined range.

The one or more electroporating signals may be each associated with an electric field. The device may further comprise a potentiometer coupled to the power supply and the electrodes. The potentiometer may be configured to maintain the electric field to about 1300 V/cm.

The power supply may be associated with an output power. The device may further comprise a potentiometer coupled to the power supply and the electrodes. The potentiometer may be configured to adjust the output power in response to the cover area of the electrodes.

The power supply may be associated with an output power. The device may further comprise a potentiometer coupled to the power supply and the electrodes. The potentiometer may be configured to reduce the output power in response to a reduced cover area of the electrodes.

The power supply may be associated with an output power. The device may further comprise a potentiometer coupled to the power supply and the electrodes. The potentiometer may be configured to increase the output power in response to an increased cover area of the electrodes.

The one or more electroporating signals may be each associated with an electric field. The device may further comprise a potentiometer coupled to the power supply and the electrodes. The potentiometer may be configured to maintain the electric field within a predetermined range so as to substantially prevent permanent damage in the cells within the cover area.

The one or more electroporating signals may be each associated with an electrical field. The device may further comprise a potentiometer coupled to the power supply and the electrodes. The potentiometer may be configured to maintain the electrical field within a predetermined range so as to substantially minimize pain.

The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

The power supply may be associated with an output power. The device may further comprise a potentiometer coupled to the power supply and the electrodes. The guide member may be slidably coupled to the applicator. The potentiometer may be configured to adjust the output power in response to the cover area of the electrodes.

The potentiometer may be configured to reduce the output power in response to a reduced cover area of the electrodes. The potentiometer may be configured to increase the output power in response to an increased cover area of the electrodes. The one or more electroporating signals may be each associated with an electric field and the potentiometer may be configured to maintain the electric field to about 1300 V/cm.

The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

The present invention is also directed to method of electroporating cells using an electroporation device. The electroporation device may comprise an applicator, a plurality of electrodes extending from the applicator, a power supply in electrical communication with the electrodes, and a guide member coupled to the electrodes. The electrodes may be associated with a cover area. The power supply may be configured to generate one or more electroporating signals to cells within the cover area. The guide member may be configured to adjust the cover area of the electrodes.

The method may comprise administering selected molecules into the cells within the cover area, contacting the cells with the electrodes, and delivering the one or more electroporating signals. The method may further comprise adjusting the cover area of the electrodes.

The one or more electroporating signals may be each associated with an electric field. Delivering the one or more electroporating signals may further comprise maintaining the electrical field within a predetermined range so as to substantially prevent permanent damage in the cells within the cover area.

The one or more electroporating signals may be each associated with an electrical field. Delivering the one or more electroporating signals may further comprise maintaining the electrical field within a predetermined range so as to substantially minimize pain. The method may further comprise adjusting a temperature of the cells to about 4° C. to about 45° C.

The present invention is also directed to an electroporation device comprising an applicator, a plurality of electrodes extending from the applicator, a power supply in electrical communication with the electrodes, and a camera coupled to the applicator and positioned adjacent the electrodes. The device may further comprise a device memory in electronic communication with the camera. The device memory may be configured to store an electroporation treatment database.

The present invention is also directed to an electroporation device comprising an applicator, a plurality of electrodes extending from the applicator, a power supply in electrical communication with the electrodes, and a cooling/heating element coupled to the applicator and positioned adjacent the electrodes. The power supply may provide a first electrical signal to a first electrode and a second electrical signal to a second electrode. The first and second electrical signals may combine to produce a wave having a beat frequency. The first and second electrical signals may each have at least one of a unipolar waveform and a bipolar waveform. The first electrical signal may have a first frequency and a first amplitude. The second electrical signal may have a second frequency and a second amplitude. The first frequency may be different from or the same as the second frequency. The first amplitude may be different from or the same as the second amplitude.

The cooling/heating element may include a Peltier cooler. The cooling/heating element may be configured to adjust a temperature of tumor cells to about 4° C. to about 45° C.

Other aspects of the invention will become apparent by consideration of the detailed description and accompanying drawings.

BRIEF DESCRIPTION OF THE DRAWINGS

FIG. 4b is a cross-sectional view of the applicator of FIG. 4a.

DETAILED DESCRIPTION

The inventors have discovered a new type of electroporation device that can cover or accommodate tumors of various sizes. The electroporation device may adjust electric signals in response to a cover area of electrodes, so that the pain from the electric signals may be tolerable when the electric signals are delivered to cells within the cover area. The electric signals may include opposing waveforms that produce a resultant interference waveform to effectively target the cover area. Each opposing waveform may be a unipolar waveform or a bipolar waveform. The resultant interference waveform may be shaped to the tumor and the voltage may vary across the tumor, for example, less voltage at a periphery of the tumor and more voltage at a central portion of the tumor.

Moreover, the electroporation device may include a camera to measure a size of the tumor and to better place the electrode needles. Furthermore, the electroporation device may include a cooling/heating element to adjust a temperature of a surface of the tumor. The invention thus provides an apparatus and a method for the therapeutic application of electroporation while minimizing tissue damage and the pain experienced by the patient.

I) ELECTROPORATION DEVICE

Figure 2:
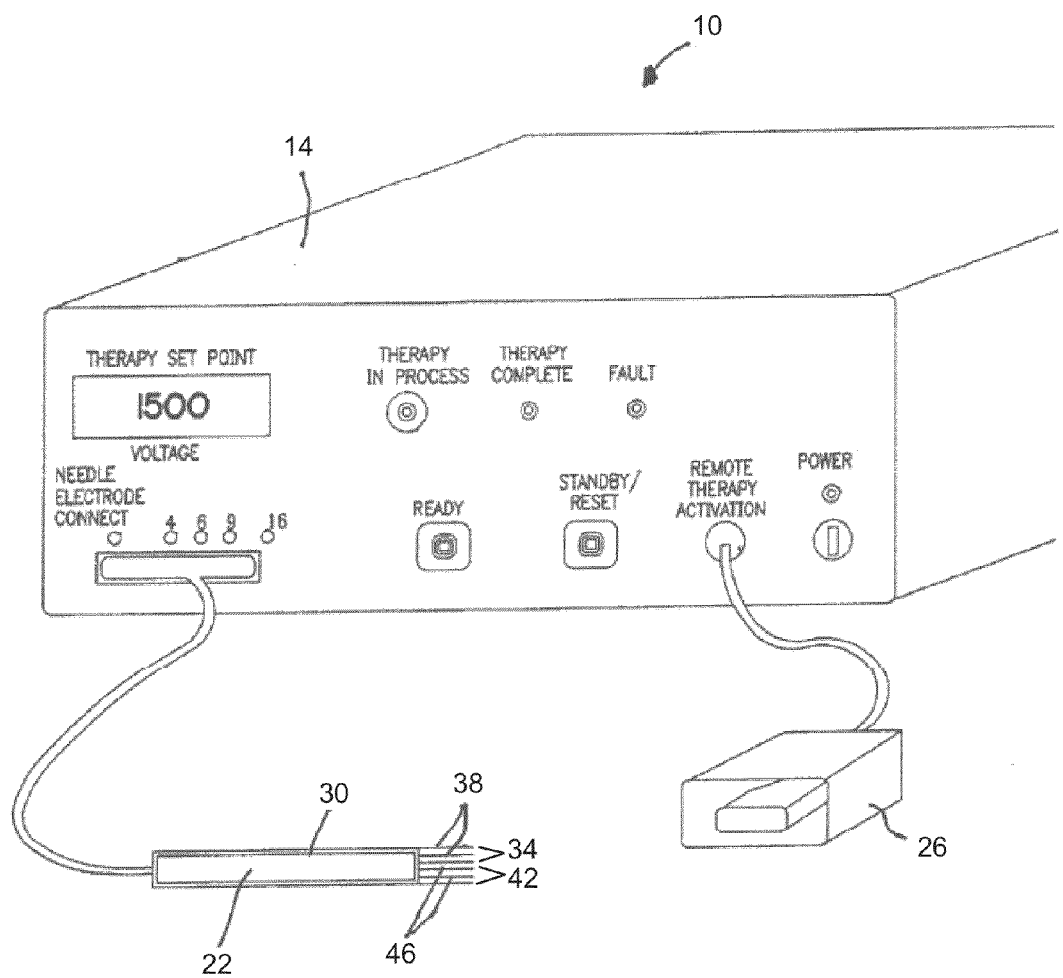
FIG. 2 is a perspective view of an electroporation device illustrating an applicator according to another embodiment.
Figure 3:
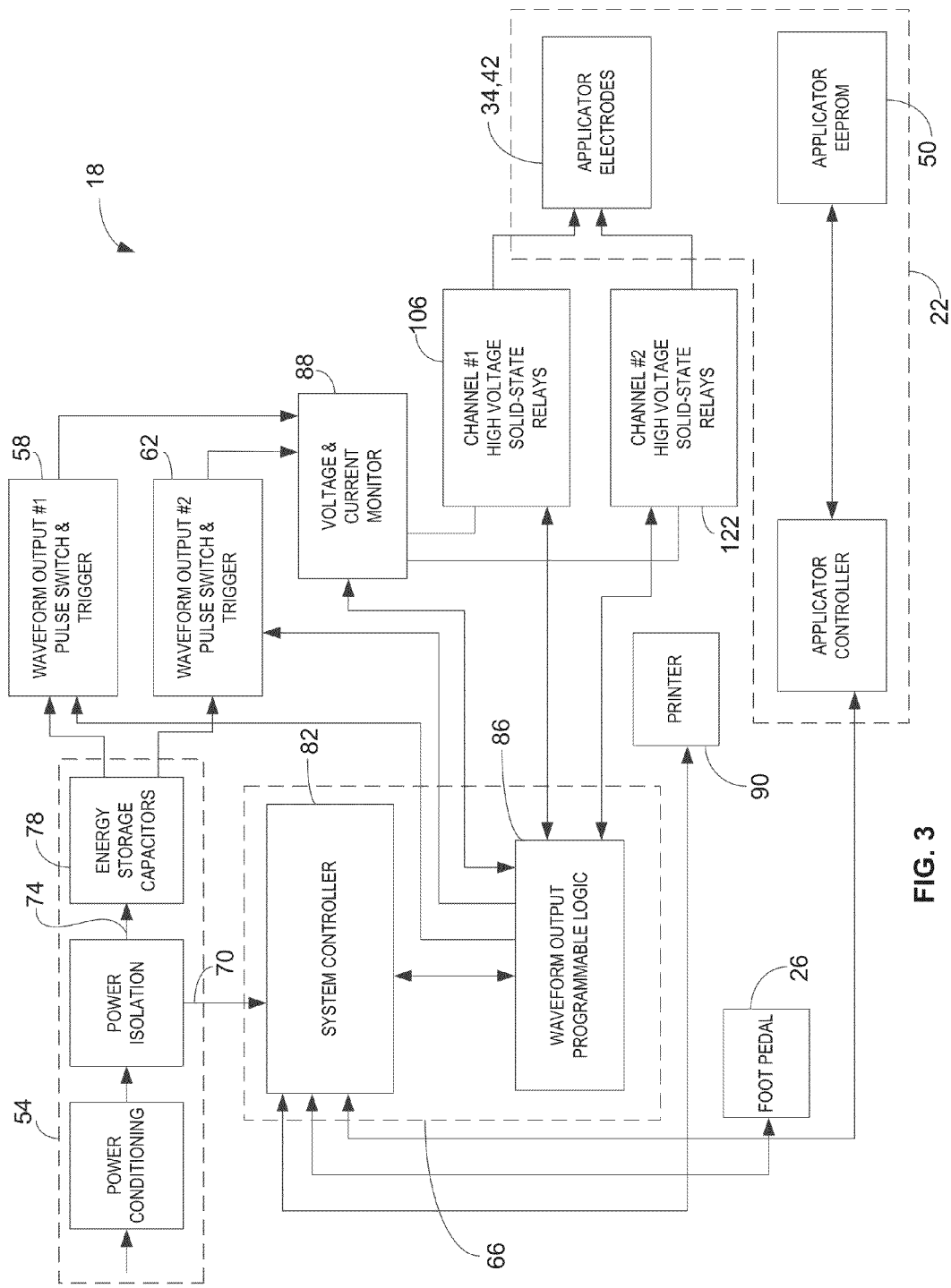
FIG. 3 is a schematic of circuitry of the electroporation device of FIG. 2.

The electroporation device 10 of the present invention includes a housing 14 (FIG. 2) containing circuitry (FIG. 3), an electrode applicator 22, 200 removably coupled to the housing 14 (FIG. 2), and a foot pedal 26 coupled to the housing 14 and in electrical communication with the circuitry 18 (FIG. 3). A remote therapy activation connection may be provided to accommodate the foot pedal 26 for activating pulses to the electrode applicator 22, 200. The foot pedal 26 may permit a physician to activate the electroporation device 10 while freeing both hands for positioning of the electrode applicator 22, 200 in a patient's tissue. Indicator lights for fault detection, power on, and completion of a therapy session may be provided for convenience. Other indicator lights may be provided to positively indicate that the electrode applicator 22, 200 is connected to the electroporation device 10 and to indicate the type of needle array. A standby/reset button may be provided to pause the electroporation device 10 and reset all functions of the electroporation device 10 to a default state. A ready button may be provided to prepare the electroporation device 10 for a therapy session. A "therapy in process" indicator light may indicate that voltage pulses are being applied to the electrode applicator 22, 200. In addition, the electroporation device 10 may have audio indicators for such functions as a button press, a fault state, commencement or termination of a therapy session, indication of therapy in process, etc. In some embodiments, the electroporation device 10 can be coupled to a feedback sensor that detects heart beats. Applying pulses near the heart may interfere with normal heart rhythms. By synchronizing application of pulses to safe periods between beats, the possibility of such interference may be reduced.

Figure 1:
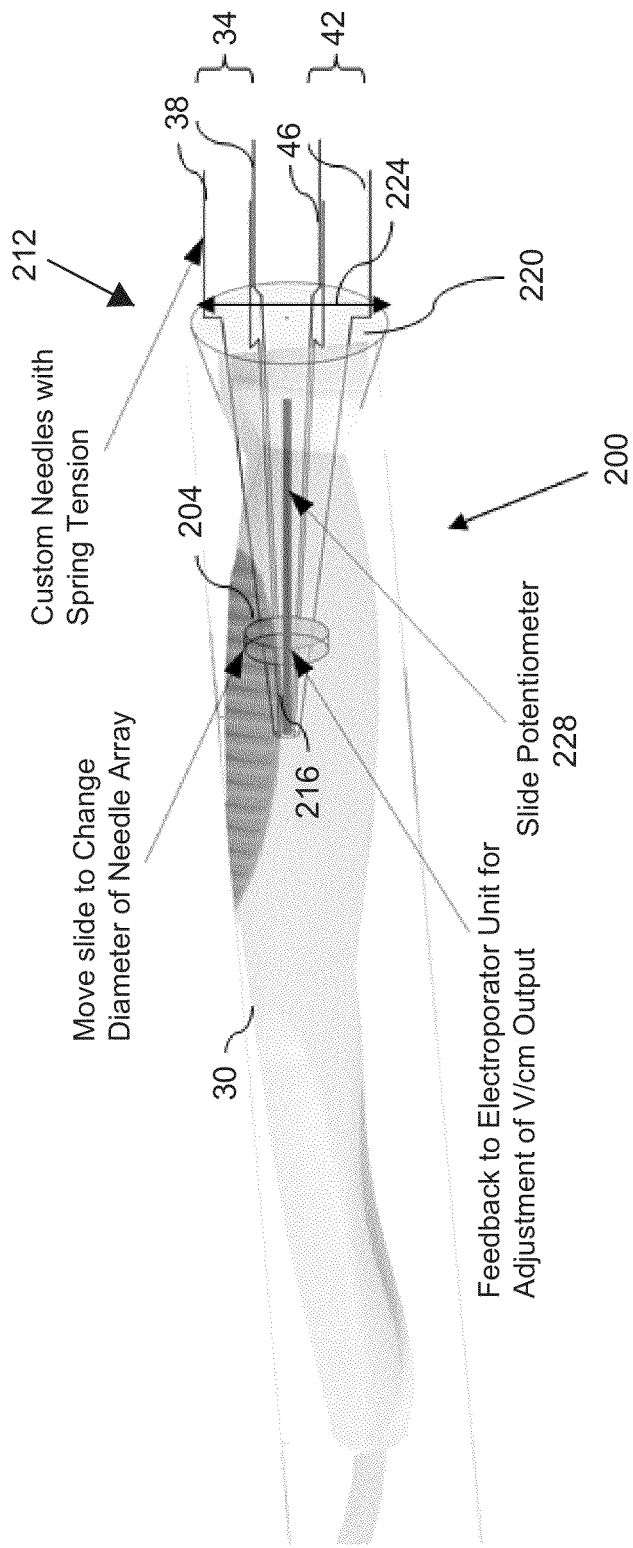
FIG. 1 is a cross-sectional view of an applicator of the electroporation device according to one embodiment.

Referring to FIG. 1, the illustrated electrode applicator 200 includes a body 30, a first electrode 34 having a first set of electrode needles 38, and a second electrode 42 having a second set of electrode needles 46. During operation, the user can manually manipulate the electrode applicator 22 to place the electrode needles 38, 46 in physical contact with the target area of the tissue. The illustrated electroporation device 10 includes a potentiometer 228 that is configured to adjust an electric output power in response to a cover area 220 of the electrodes 34, 42, thereby maintaining an electric field of the electric signals substantially within a predetermined range.

A) Electrode Applicator

Referring to FIG. 1, in the illustrated embodiment, a guide member 204 is coupled to the electrodes 34, 42. The electrodes 34, 42 are associated with the cover area 220. A power supply is configured to generate one or more electroporating signals 94, 110 to cells within the cover area 220. The guide member 204 is configured to adjust the cover area 220 of the electrodes 34, 42. In the illustrated embodiment, the guide member 204 is in the form of a ring. In other embodiments, the guide member 204 can instead include portions of a ring, arcuate members, and the like that can suitably adjust the cover area 220 of the electrodes 34, 42.

In the illustrated embodiment, the guide member 204 is coupled to the electrode applicator 200. The electrode applicator 200 is associated with an applicator end 212, and sliding the guide member 204 toward the applicator end 212 decreases the cover area 220 of the electrodes 34, 42. For example, each electrode 34, 42 may be needle-shaped, and include spring tension at an end distal to the applicator end 212. In the illustrated embodiment, the electrodes 34, 42 are positioned within the electrode applicator 200 in a conical arrangement. The conical arrangement of the electrodes 200 is associated with an apex or tip 216, where individual electrodes 34, 42 are connected to one another in a tight bundle, and the cover area 220 positioned away from the apex or tip 216. In some embodiments, the cover area 220 may assume any geometric form, including, but not limited to, a circle associated with a diameter 224, an oval, an ellipse, a lens, a squircle, a polygon, a symbol, or a combination thereof.

In the illustrated embodiment, for example, as the guide member 204 is moved toward the applicator end 212, the spring-tensioned electrodes 34, 42 are drawn radially inward within the conical arrangement, thereby reducing the base diameter 224. On the other hand, sliding the guide member 204 away from the applicator end 212 increases the base diameter 224, thereby increasing the cover area 220. Although FIG. 1 illustrates the guide member 204 as being slidably coupled to the electrode applicator 200, in other embodiments, the guide member 204 may be coupled to the electrode applicator 200 using other mechanisms.

In the illustrated embodiment, the potentiometer 228 is coupled to the power supply and the electrodes 34, 42. The power supply is associated with an output power, and the potentiometer 228 is configured to adjust the output power in response to the cover area 220 of the electrodes 34, 42. For example, in the illustrated embodiment, sliding the guide member 204 toward and away from the applicator end 212 can provide feedback to the power supply regarding the associated base diameter 224 or cover area 220, so that the output power can be adjusted accordingly. In the illustrated embodiment, the potentiometer 228 is electrically insulated from the guide member 204 and supports the guide member 204 during travel. The potentiometer 228 is configured to reduce the output power in response to a reduced base diameter 224 or cover area 220 of the electrodes 34, 42, and increase the output power in response to an increased base diameter 224 or cover area 220 of the electrodes 34, 42. In other embodiments, the potentiometer 228 may be configured to adjust the output power using other mechanisms.

The electroporating signals 94, 110 are each associated with an electric field, and in some embodiments the potentiometer 228 is configured to maintain the electric field substantially within a predetermined range so as to substantially prevent permanent damage in the cells within the cover area 220 and to minimize the amount of pain experienced by the user. For example, the potentiometer 228 can be configured to maintain the electric field to about 1.300 kV/cm. In some embodiments, the potentiometer is configured to maintain the electric field to at least 375 V/cm, at least 450 V/cm, at least 525 V/cm, at least 600 V/cm, at least 675 V/cm, at least 750 V/cm, at least 825 V/cm, at least 900 V/cm, at least 975 V/cm, at least 1.000 kV/cm, at least 1.075 kV/cm, at least 1.150 kV/cm, or at least 1.225 kV/cm. In further embodiments, the potentiometer 228 is configured to maintain the electric field to no more than 1.300 kV/cm, no more than 1.225 kV/cm, no more than 1.150 kV/cm, no more than 1.075 kV/cm, no more than 1.000 kV/cm, no more than 925 V/cm, no more than 850 V/cm, no more than 775 V/cm, no more than 750 V/cm, no more than 675 V/cm, no more than 600 V/cm, no more than 525 V/cm, or no more than 450 V/cm. In other embodiments, the potentiometer 228 may be configured to maintain the electric field as other values.

Figure 5:
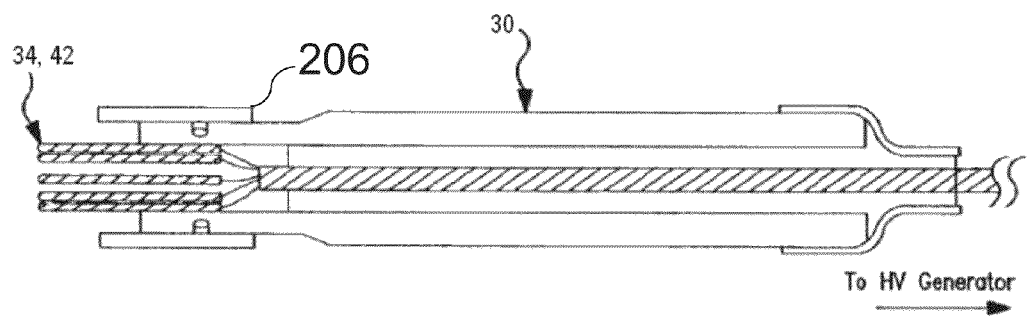
FIG. 5 is a cross-sectional view of an applicator of the electroporation device of FIG. 2, illustrating a retractable shield.

FIGS. 2 and 5 illustrate an electrode applicator of an electroporating device according to another embodiment. This embodiment employs much of the same structure and has many of the same properties as the embodiment of the electroporation device described above in connection with FIG. 1. Accordingly, the following description focuses primarily upon the structure and features that are different than the embodiment described above in connection with FIG. 1. Structure and features of the embodiment shown in FIG. 1 that correspond to structure and features of the embodiment of FIGS. 2 and 5 are designated hereinafter with like reference numbers.

The guide member 206 in this embodiment is a retractible shield. The retractible shield 206 may be restricted by a friction O-ring (not shown) near a distal end of the body 30 of the electrode applicator 22, and can be slid fore and aft along the body 30 to protect or expose the first and second electrodes 34, 42. Thus, the retractible shield 206 is configured to adjust the cover area 208 of the first and second electrodes 34, 42 to accommodate tumors of various sizes.

Because it is possible for a number of different electrode applicator 22 designs to be attached to the electroporation device 10, the electrode applicator 22 includes an electrically erasable programmable read-only memory (EEPROM) chip 50 (FIG. 3) with profile data stored thereon. The profile data is unique to each specific applicator and may include information regarding the model, the make, the number of electrodes present, and instructions for a desired treatment. In use, the electroporation device 10 can read the EEPROM chip 50 to assure the proper settings are being used for each particular type of electrode applicator 22.

B) Integrated Wide-Angle Camera Applicator

Figure 6:
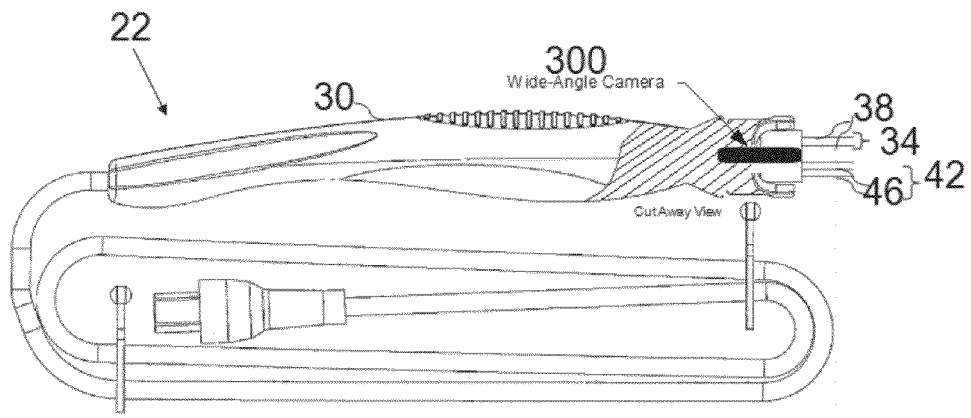
FIG. 6 is a cut-away view of an applicator of the electroporation device according to yet another embodiment.

Referring to FIG. 6, in the illustrated embodiment, a small or miniature wide-angle camera 300 is embedded or integrated in the electrode applicator 22 between the electrode needles 38, 46. In some embodiments, this camera 300 may interface with an onboard electroporator software to acquire details regarding a tumor, such as type, size, shape, color, condition, and progression during electroporation therapy (EPT). The electroporator software may display an image transmitted from the camera 300, so that a clinician or medical professional performing EPT can determine tumor treatment coverage. In further embodiments, the tumor may be displayed with a visible grid. The clinician may then utilize visual analysis algorithms to measure a size of the tumor and to better place the electrode needles 38, 46, thereby ensuring a complete electroporation coverage. As explained below, in some embodiments, the electroporator software may also record a patient number (not necessarily including patient's personal information), dates of treatments, waveform parameters, needle placement, and therapeutic agent dosage.

C) Integrated Thermoelectric Cooler/Heater Applicator

Figure 7:
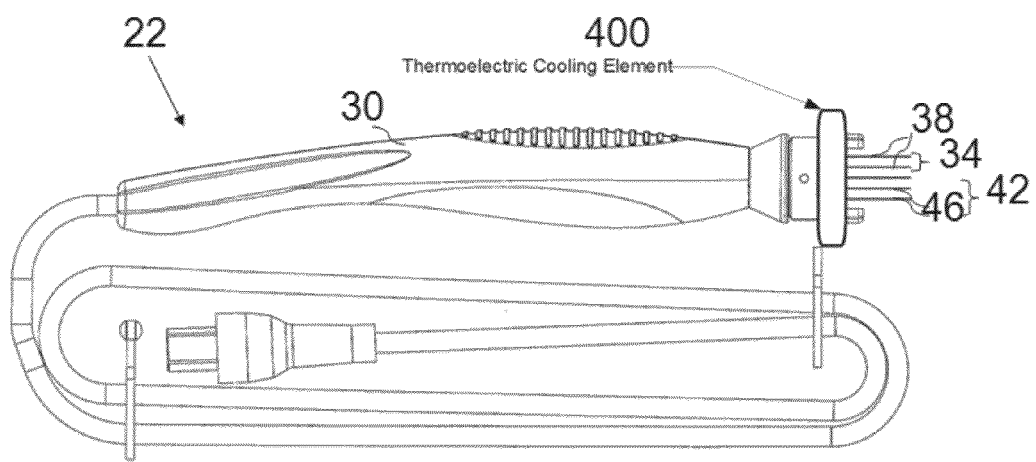
FIG. 7 is a plan view of an applicator of the electroporation device according to still another embodiment.

Referring to FIG. 7, in the illustrated embodiment, a small or miniature thermoelectric cooling/heating element 400 is included or integrated in the electrode applicator 22. The illustrated thermoelectric cooling/heating element 400 is located at a distal end of the electrode applicator 22. In some embodiments, the thermoelectric cooling/heating element 400 may provide non-contact or radiant pre-cooling/heating to a surface of the tumor. In other embodiments, however, the thermoelectric cooling/heating element 400 may provide contact cooling/heating to a surface of the tumor.

Lowering a temperature of the tumor cells before electroporation to about 4° C. may improve the transfection of the therapeutic agent about ninefold. Thus, the thermoelectric cooling/heating element 400 can reduce the temperature of the solid tumor body, and thereby improve transfection. In some embodiments, the thermoelectric cooling/heating element 400 can reduce the temperature of the tumor cells before EPT to about 45° C., to about 44° C., to about 43° C., to about 42° C., to about 41° C., to about 40° C., to about 39° C., to about 38° C., to about 37° C., to about 36° C., to about 35° C., about 34° C., about 33° C., about 32° C., about 31° C., about 30° C., about 29° C., about 28° C., about 27° C., about 26° C., about 25° C., about 24° C., about 23° C., about 22° C., about 21° C., about 20° C., about 19° C., about 18° C., about 17° C., about 16° C., about 15° C., about 14° C., about 13° C., about 12° C., about 11° C., about 10° C., about 9° C., about 8° C., about 7° C., about 6° C., about 5° C., or about 4° C. In some embodiments, the thermoelectric cooling/heating element 400 can increase the temperature of the tumor cells before electroporation to about 38° C., about 39° C., about 40° C., about 41° C., about 42° C., about 43° C., about 44° C., or about 45° C. Thus, the thermoelectric cooling/heating element 400 can adjust the temperature of the tumor cells before EPT to about 4° C. to about 45° C., to about 33° C. to about 45° C., to about 4° C. to about 40° C., or to about 33° C. to about 40° C.

In some embodiments, the thermoelectric cooling/heating element 400 may include a Peltier cooler. A Peltier cooler is a solid-state active heat pump creating a heat flux between a junction of two different types of materials. The heat is thereby transferred from one material to the other, with consumption of electrical energy, depending on the direction of the current. In other embodiments, the thermoelectric cooling/heating element 400 may utilize other cooling mechanisms. In operation, the clinician may move the distal end of the electrode applicator 22 close to the tumor before beginning EPT, and lower the temperature of the tumor tissue through radiant cooling. The reduced tumor temperature may increase the percentage of therapeutic agent transfer into the cells. In some embodiments, the thermoelectric cooling/heating element 400 may be powered by the same power supply as the electrode applicator 22.

D) Electroporation Treatment Database

In some embodiments, an electroporation device memory (not shown) may store data such as tumor type, photographic record of tumor size, color, shape, tumor progression, therapeutic agent dosage, electroporation parameters, and needle insertion placement. In further embodiments, this data may be collected into the electroporation device memory and downloaded, e.g., periodically, via a wireless connection to a cloud storage database (not shown). This may facilitate the creation of a novel database which can be developed to answer questions about future EPT protocols or aspects of the treatment unknown at this time. In some embodiments, this information may not include patient personal information, but instead include a patient number. In further embodiments, patient sex, age, location, treating physician, tumor type, photographic record of tumor size, color, shape, tumor progression, therapeutic agent dosage, EPT parameters, needle insertion placement, etc., may be collected and included in the database.

E) Electrical Signals

The electroporation device 10 as disclosed herein is operable to provide an unlimited variety of electric signals so long as the pain from the electric signals is tolerable. In some embodiments, the electroporation device 10 is operable to separately apply pulses of high amplitude electric signals to at least two pairs of the first and second electrodes 34, 42. The electric signals may be applied proportionately to the distance between the electrodes of a pair to generate a nominal field strength of about 10 V/cm to about 1500 V/cm in the cells and effect introduction of selected molecules into the cells without permanently damaging the cells. In some embodiments, the electric signals may be applied simultaneously. In further embodiments, the electric signals may be applied to some, but not all electrodes.

Figure 11:
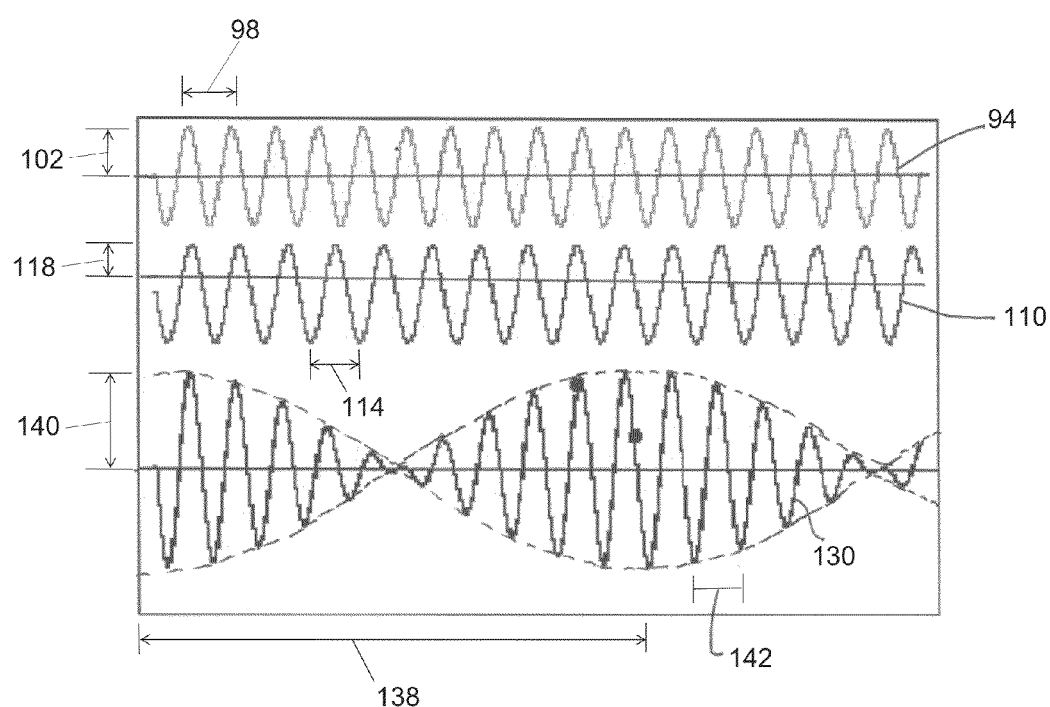
FIG. 11 is a graph plotting waveforms produced by the electroporation device of FIG. 2.

Referring to FIG. 11, in some embodiments, the electroporation device 10 sends multiple, independent electric signals during operation to selected electrode needles 34, 42 that, when in contact with tissue, can cause electroporation in the cell wall. That is, a power supply (not shown) may provide a first electrical signal 94 to the first electrode 34 and a second electrical signal 110 to the second electrode 42. When the first and second electrodes 34, 42 are in electrical contact with a biological sample, the first electrical signal 94, which has a first frequency (corresponding to the wavelength 18 in FIG. 11), and the second electrical signal 110, which has a second frequency (corresponding to the wavelength 114 in FIG. 11), different or the same from the first frequency (the first and second signals may have amplitudes that are different or the same), combine to produce a resultant wave 130 that may include a beat frequency and an embedded frequency to effect introduction of selected molecules into cells of the sample without permanently damaging the cells and minimizing pain. In other embodiments, however, the power supply of the electroporation device 10 may adjust the electrical signals for all electrodes 34, 42 in unison. That is, the electrical signals for one electrode may not be independent of other electrodes, and the electrical signals 94, 110 may not produce a beat frequency.

The nature of the tissue, the size of the selected tissue, and its location determine the nature of the electric signals 94, 110 to be generated. It is desirable that the field be as homogenous as possible and of the correct amplitude. An excessive field strength may result in lysis of cells, whereas a low field strength may result in a reduced efficiency of delivering agents into the cell. This is especially true in the present invention where the resultant or resulting wave 130 (e.g., the waveform experienced by the patient during therapy) is the result of the interference of the first and second electrical signals 94, 110. As such, any minor variances in the first and second signals 94, 110 could result in major variances in the resulting wave 130.

As illustrated in FIG. 11, the first electrical signal 94 may include a sinusoidal, cosinusoidal or pulsed electrical wave having a first frequency (corresponding to the wavelength 98 in FIG. 11) and the first amplitude 102. The electrical signal may be monopolar or bi-polar dependent upon the specific treatment being administered. In some embodiments, the first frequency is generally between about 500 Hz and about 10,000 Hz. In other embodiments, the first frequency is between about 600 Hz and about 9,000 Hz. In still other embodiments, the first frequency is between 700 Hz and about 8,000 Hz. In still other embodiments, the first frequency is between about 800 Hz and about 7,000 Hz. In still other embodiments, the first frequency is between about 900 Hz and about 6,000 Hz. In still other embodiments, the first frequency is between about 1,000 Hz and about 5,000 Hz. In still other embodiments, the first frequency is between about 2,000 Hz and about 4,000 Hz. Furthermore, the first amplitude 102 is generally between about 150 V and about 3,000 V. In other embodiments, the first amplitude 102 is between about 250 V and about 2,000 V. In still other embodiments, the first amplitude 102 is between about 350 V and about 1,000 V. In still other embodiments, the first amplitude 102 is between about 450 V and about 900 V. In still other embodiments, the first amplitude 102 is between about 550 V and about 800 V. In the case of a pulsed electrical wave, the first electrical signal 94 may produce from about 500 pulses per second to about 10,000 pulses per second.

As illustrated in FIG. 11, the second electrical signal 110 may include a sinusoidal or cosinusoidal electrical wave having a second frequency (corresponding to the wavelength 114 in FIG. 11) different from the first frequency and a second amplitude 118 substantially similar to the first amplitude 102. The second electrical signal 110 may be monopolar or bi-polar dependent upon the type of treatment being administered. In some embodiments, the second frequency is generally between about 500 Hz and about 10,000 Hz. In other embodiments, the second frequency is between about 600 Hz and about 9,000 Hz. In still other embodiments, the second frequency is between 700 Hz and about 8,000 Hz. In still other embodiments, the second frequency is between about 800 Hz and about 7,000 Hz. In still other embodiments, the second frequency is between about 900 Hz and about 6,000 Hz. In still other embodiments, the second frequency is between about 1,000 Hz and about 5,000 Hz. In still other embodiments, the second frequency is between about 2,000 Hz and about 4,000 Hz. Furthermore, the second amplitude 118 is generally between about 150 V and about 3,000 V. In other embodiments, the second amplitude 118 is between about 250 V and about 2,000 V. In still other embodiments, the second amplitude 118 is between about 350 V and about 1,000 V. In still other embodiments, the second amplitude 118 is between about 450 V and about 900 V. In still other embodiments, the second amplitude 118 is between about 550 V and about 800 V. In the case of a pulsed electrical wave, the second electrical signal 110 may produce from about 500 pulses per second to about 10,000 pulses per second.

Illustrated in FIG. 11, the resultant wave 130 is the result of the combined interference of the first electrical signal or wave 94 and the second electrical signal or wave 110. Governed by the laws of wave interference, the resultant wave 130 may include a beat frequency, defined as the frequency of the oscillation of the envelope of the resultant wave 130 (corresponding to a wavelength 138 in FIG. 11). The resultant wave 130 may also include an embedded frequency defined as the frequency of the carrier wave (corresponding to a wavelength 142 in FIG. 11). In the illustrated embodiment, the beat frequency is between about 2 Hz and about 3,000 Hz. In other embodiments, the beat frequency is between about 50 Hz and about 2,000 Hz. In still other embodiments the beat frequency is between about 100 Hz and about 1,000 Hz. In still other embodiments, the beat frequency is between about 200 Hz and about 900 Hz. In still other embodiments, the beat frequency is between about 300 Hz and about 800 Hz. In still other embodiments, the beat frequency is between about 400

Hz and about 700 Hz. Furthermore, the embedded frequency is from about 500 Hz to about 10,000 Hz. In other embodiments, the embedded frequency is between about 600 Hz and about 9,000 Hz. In still other embodiments, the embedded frequency is between 700 Hz and about 8,000 Hz. In still other embodiments, the embedded frequency is between about 800 Hz and about 7,000 Hz. In still other embodiments, the embedded frequency is between about 900 Hz and about 6,000 Hz. In still other embodiments, the embedded frequency is between about 1,000 Hz and about 5,000 Hz. In still other embodiments, the embedded frequency is between about 2,000 Hz and about 4,000 Hz. An amplitude 140 of the resultant wave 130 is generally equal to the sum of the amplitudes of the interfering waves (e.g., the first wave and the second wave corresponding to the first and second electrical signals 94, 110). In the case of a pulsed wave, the beat frequency of the resultant wave 130 is from about 2 pulses per second (Hz) to about 3,000 pulses per second (Hz).

Figure 12A:
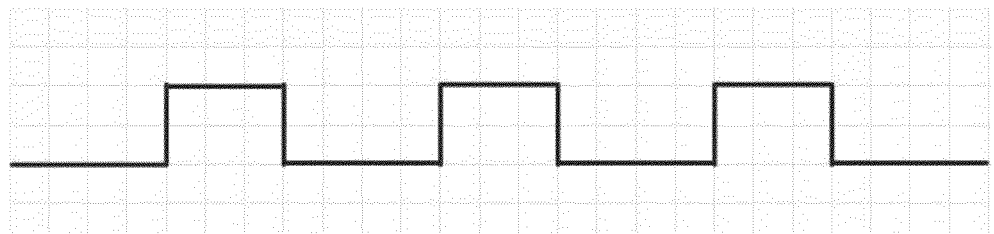
FIGS. 12a-12c are schematic illustrations of opposing unipolar waveforms and the resultant unipolar interference waveform, produced by the electroporation device of FIG. 2.
Figure 12B:
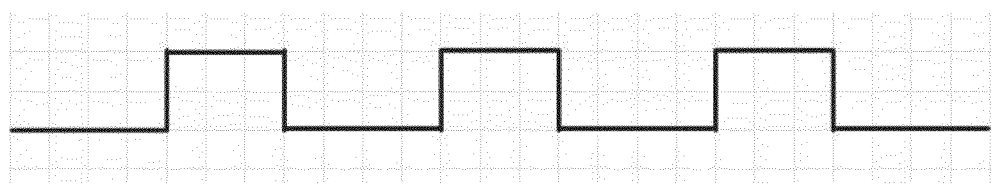
Figure 12C:
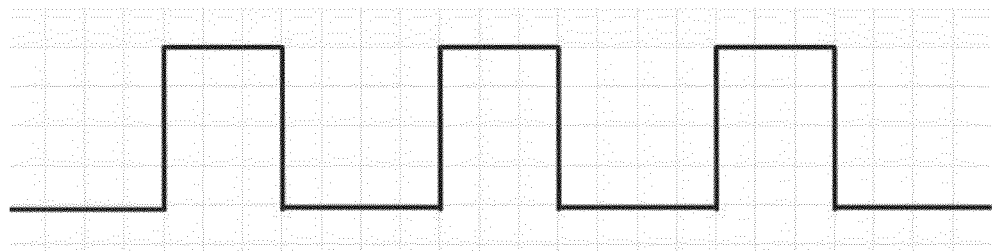

It is to be understood that although the above described wave forms are sinusoidal or cosinusoidal in nature, square waves, saw tooth waves, step waves, and the like may also be produced by the electroporation device 10. Referring also to FIG. 12, each opposing waveform may be a unipolar waveform or a bipolar waveform. When each opposing waveform is unipolar (e.g., square wave) as illustrated in FIGS. 12*a* and 12*b*, the result interference waveform is also unipolar as illustrated in FIG. 12*c*. The amplitude of the illustrated resultant wave is generally equal to the sum of the amplitudes of the opposing waves, and the beat frequency may be defined as the pulse frequency of the resultant square wave.

In some embodiments, the resultant wave 130 may be the result of the interference of more than two wave forms. The specific waveforms produced by the electroporation device 10 are designed to produce the desired electroporation effect in the cell wall while minimizing the amount of pain experienced by the user, minimizing tissue damage, and providing maximum pore formation for introducing an agent into a cell.

Figures 13A, 13B, 13C:
FIGS. 13a-13c are schematic illustrations of two waveforms and the resultant interference waveform, produced by the electroporation device of FIG. 2.

As illustrated in FIGS. 13*a*-13*c*, two separate waveforms (i.e., signals 1 and 2) may combine or interfere such that the resultant waveform has a specific shape. The shape of the resultant waveform may be similar to (or the same as) the shape of the tissue or cells targeted for electroporation. Accordingly, the electroporation effect is directed to the targeted tissue or cells and not surrounding or other tissues, thereby minimizing tissue damage in the user. The waveforms may be varied such that the resultant waveform has any desired shape, and therefore, the electroporation effect may be produced in tissues or areas of treatment having different shapes and sizes. The electroporation effect may be shaped to the tissue or area of treatment.

Additionally, the voltage at the intersection of the two waveforms may be the sum of the voltages of the two waveforms. For example, if both the first and second waveforms have a voltage of 650 V, then at the intersection of the first and second waveforms, the voltage would be 1300 V. The waveforms may each have a lower voltage, but combine or interfere to provide the higher voltage needed for maximum pore formation for introducing the agent into a cell. These lower voltage waveforms have a higher frequency, which in turn, reduces impedance through the tissue, decreases tissue damage, and minimizes pain experienced by the user.

The waveforms may also combine such that the resultant waveform has a shape matching the targeted tissue and the voltage varies across the targeted tissue. For example, if the targeted tissue is a tumor, the resultant waveform may have a shape similar to (or the same as) a shape of the tumor, but because the voltage varies across the tumor shape, different portions of the tumor are exposed to more or less voltage (e.g., less voltage at a periphery portion of the tumor and higher voltage at a central portion of the tumor). The electroporation effect may be shaped to the tissue or area of treatment while a spectrum of voltages is present in the tissue or area of treatment. This in turn allows the electroporation effect to be directional to minimize tissue damage and pain experienced by the user while maximizing pore formation for the introduction of the agent into the cell.

F) Signal Generation

Illustrated in FIG. 3, the circuitry 18 of the electroporation device 10 includes an AC power module 54, a first waveform generator 58, a second waveform generator 62, and a control module 66. In some embodiments, the circuitry 18 of the electroporation device 10 produces a beat wave 130 (FIG. 11). The beat wave 130 is designed to produce electroporation in the cell while minimizing the amount of pain experienced by the patient.

The AC power module 54 of the circuitry 18 receives electricity from a power source (e.g., from a wall socket, a generator, and the like), conditions the signal, and isolates the signal into multiple power sources to be used as electrical power throughout device. More specifically, the AC power module 54 produces a low-voltage DC power supply 70 suitable for use by the control module 66, and a high voltage power supply 74 (e.g., up to several thousand volts) suitable for waveform generation. In the illustrated construction, the AC power module 54 utilizes a large toroidal transformer to isolate and condition the power source signal.

The AC power module 54 also includes a plurality of capacitors 78 to store the high voltage power supply 74 for use by the first and second waveform generators 58, 62. In the illustrated embodiment, pulse width modulation is used to control the high voltage power supply 74 so it better accommodates therapy and delivery requirements.

The control module 66 of the interior circuitry 18 includes a microprocessor 82 and a custom programmable logic array (PLA) 86. The PLA 86 of the current invention independently controls the first and second waveform generators 58, 62. Stated differently, the PLA 86 is pre-programmed with multiple sets of waveform profiles, each corresponding to a unique therapy or treatment. During operation, the microprocessor 82 sends a signal to the PLA 86 instructing it to produce a particular waveform profile. The PLA 86 then independently controls the first and second waveform generators 58, 62 until the signal from the microprocessor 82 is stopped. The PLA 86 also receives feedback from the produced waveforms (e.g., through a voltage and current monitor 88), to assure the waveforms are within acceptable parameters. In the event the waveforms are unacceptable or a fault is detected, the PLA 86 may shut down automatically.

Utilizing the PLA 86 independent of the microprocessor 82 ensures that the generated waveforms are not affected by the other services required by the microprocessor 82 during operation of the device. The separation also ensures the system reacts immediately to any faults or error inputs in a safe fashion.

The microprocessor 82 acts as a system controller, sending and receiving signals from various devices in the electroporation device 10. One such function of the microprocessor 82 includes determining the type of electrode applicator 22 in use. When the electrode applicator 22 is connected to the housing 14, the microprocessor 82 reads the profile data stored in the EEPROM chip 50 and uses that data to determine the proper waveform profiles the PLA 86 should produce. The microprocessor 82 also receives a signal from the foot pedal 26 and is capable of outputting data regarding the treatment to a printer or other output device 90.

The first waveform generator 58 receives high voltage electrical power from the capacitors 78 of the AC power module 54, along with input from the PLA 86, to produce a first electrical signal 94 having a first frequency (corresponding to a wavelength 98 in FIG. 11) and a first amplitude 102 (see FIG. 11). In the illustrated construction, the first waveform generator 58 utilizes an insulated gate bipolar transistor or IGBT to produce the first electrical signal 94.

The first waveform generator 58 is electrically connected to a solid-state high-voltage relay 106 to control and output the first electrical signal 94 to the desired electrode needles 38 of the first electrode 34. In the illustrated embodiment, after the waveform is produced (e.g., by the IGBT), the waveform may be checked by the PLA 86 before being passed on by the high-voltage relay 106.

The second waveform generator 62 is substantially similar to the first waveform generator 58. The second waveform generator 62 receives high voltage electrical power from the capacitors 78 of the AC power module 54, along with input from the PLA 86, to produce a second electrical signal 110 having a second frequency (corresponding to a wavelength 114 in FIG. 11), different from the first frequency, and a second amplitude 118. In the illustrated construction, the second waveform generator 62 utilizes an insulated gate bipolar transistor or IGBT to produce the second electrical signal 110.

The second waveform generator 62 is electrically connected to a solid-state high-voltage relay 122 to control and output the second electrical signal 110 to the desired electrode needles 46 of the second electrode 42. In the illustrated embodiment, after the waveform is produced (e.g., by the IGBT), the waveform may be checked by the PLA 86 before being passed on by the high-voltage relay 122.

G) Needle Array

1) Disposable Needle Array Tips

The electroporation device 10 may include disposable needle array tips. The whole needle array shown in FIG. 5 may be disposable, including the cable and the connector. However, it may be more desirable to make the needle array tip an independent component that is detachable from the body 30 and the cable. Hence, a needle array tip may be disposed after use similar to the disposable needles used in injection of a fluid drug. Such disposable needle array tips can be used to eliminate possible contamination due to improper sterilization when reusing a needle array tip.

Figure 4A:
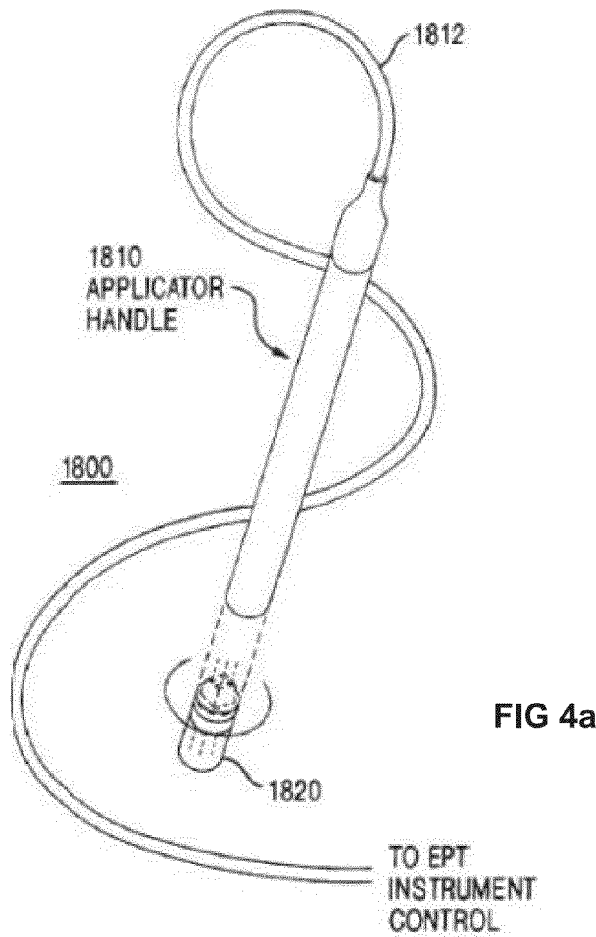
FIG. 4a is a perspective view of one embodiment of an applicator of the electroporation device of FIG. 2, illustrating a disposable needle array tip.

FIG. 4a shows one embodiment 1800 of the electroporation applicator according to this aspect of the invention. The electroporation applicator 1800 includes an applicator handle 1810, a detachable needle array tip 1820, and an applicator cable 1812 connected to the applicator handle 1810. The detachable needle array tip 1820 can be engaged to and detached from one end of the applicator handle 1810. When engaged to the applicator handle 1810, the detachable needle array tip 1820 can receive electrical signals from the electroporation device 10 through the applicator cable 1812.

Figure 4B:
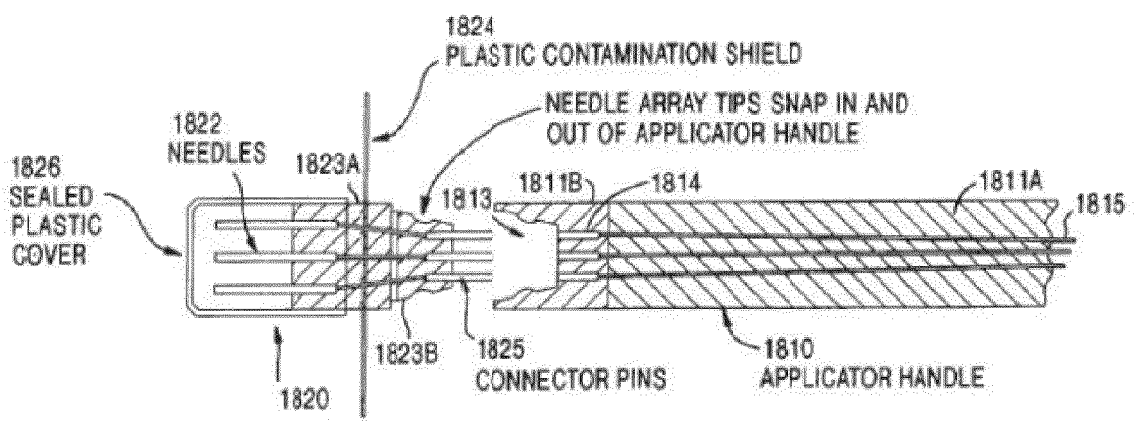

FIG. 4b shows structure details of the applicator handle 1810 and the detachable needle array tip 1820. The applicator handle 1810 includes a main body 1811A and a distal end 1811B formed on one end of the main body 1811A. The other end of the main body 1811A is connected to the applicator cable (not shown, see FIG. 4a). The main body 1811A includes two or more conducting wires 1815 for transmitting electrical signals to the detachable needle array tip 1820. These signals may include needle voltage setpoint, pulse length, pulse shape, the number of pulses, and switching sequence. In one embodiment, when the detachable needle array tip 1820 is used to deliver a liquid substance, one or more electrode needles may be made hollow for transmitting the liquid substance and one or more liquid channels may be accordingly implemented in the applicator handle 1810. The liquid channel may be integrated with one of the conducting wires 1815 by, for example, using a metal-coated plastic tube or a metal tube. Alternatively, the liquid substance may be delivered to a target by using a separate device, for example, prior to application of the electrical pulses. The distal end 1811B has an opening 1813 for engaging the needle array tip 1820. A plurality of connector holes 1814 are formed for receiving connector pins in the detachable needle array tip 1820.

The detachable needle array tip 1820 has a plurality of electrode needles 1822 forming a desired needle array, a support part 1823A that holds the electrode needles 1822, and a connector part 1823B for engaging to the applicator handle 1810. In one embodiment, when the detachable needle array tip 1820 is also used to deliver the liquid substance, at least one electrode needle is hollow and is connected to a liquid channel in the applicator handle 1810 for receiving the liquid substance. The connector part 1823B is shaped to be inserted into the opening 1813 in the distal end 1811B of the applicator handle 1810. A locking or snapping mechanism may be optionally implemented to secure the detachable needle array tip 1820 to the applicator handle 1810. A plurality of connector pins 1825 corresponding to the electrode needles 1822 are formed in the connector part 1823B for engaging to the respective connector holes 1814 in the distal end 1811B.

The detachable needle array tip 1820 may include a contamination shield 1824 formed on the support part 1823A for preventing the applicator handle 1810 from directly contacting any substance during an electroporation process. A removable plastic cover 1826 may also be formed on the support part 1823A to seal the electrode needles 1822 and maintain the sterility of the needles 1822 prior to use.

In some embodiments, the applicator handle 1810 may be configured to receive a detachable needle array tip 1820 with other numbers of electrode needles 1822. In further embodiments, an electrical identification element or EEPROM 50 may be implemented to allow the electroporation device 10 of FIG. 2 to determine the number of the electrode needles in an attached needle array tip. This identification element 50 may also be configured to generate proper electrical signal parameters corresponding to an identified needle array tip. A desired needle array addressing scheme may be selected accordingly to address the electrode needles.

2) Needle Arrays with Partially Insulated Electrode Needles

The electroporation device 10 may include needle arrays with partially insulated electrode needles. Each electrode needle in the fixed and disposable needle arrays shown in FIGS. 1, 4a, 4b, 5, 6, 7, and 8 may be partially covered with an insulator layer in such a way that only a desired amount of the tip portion is exposed. The pulsed electric fields generated by such a partially insulated needle array are primarily concentrated in regions between and near the exposed tip portions of the electrode needles during a treatment, and are small in regions between and near the insulated portions. A partially insulated needle array can be used to confine the electroporation in a targeted area with a tumor and significantly shield the skin and tissues beyond the target area from the electroporation process. This provides protection to the uninvolved skin and tissues, which are at risk because certain drugs may cause undesired or even adverse effects when injected into uninvolved surface tissue above the target area.

Figure 8:
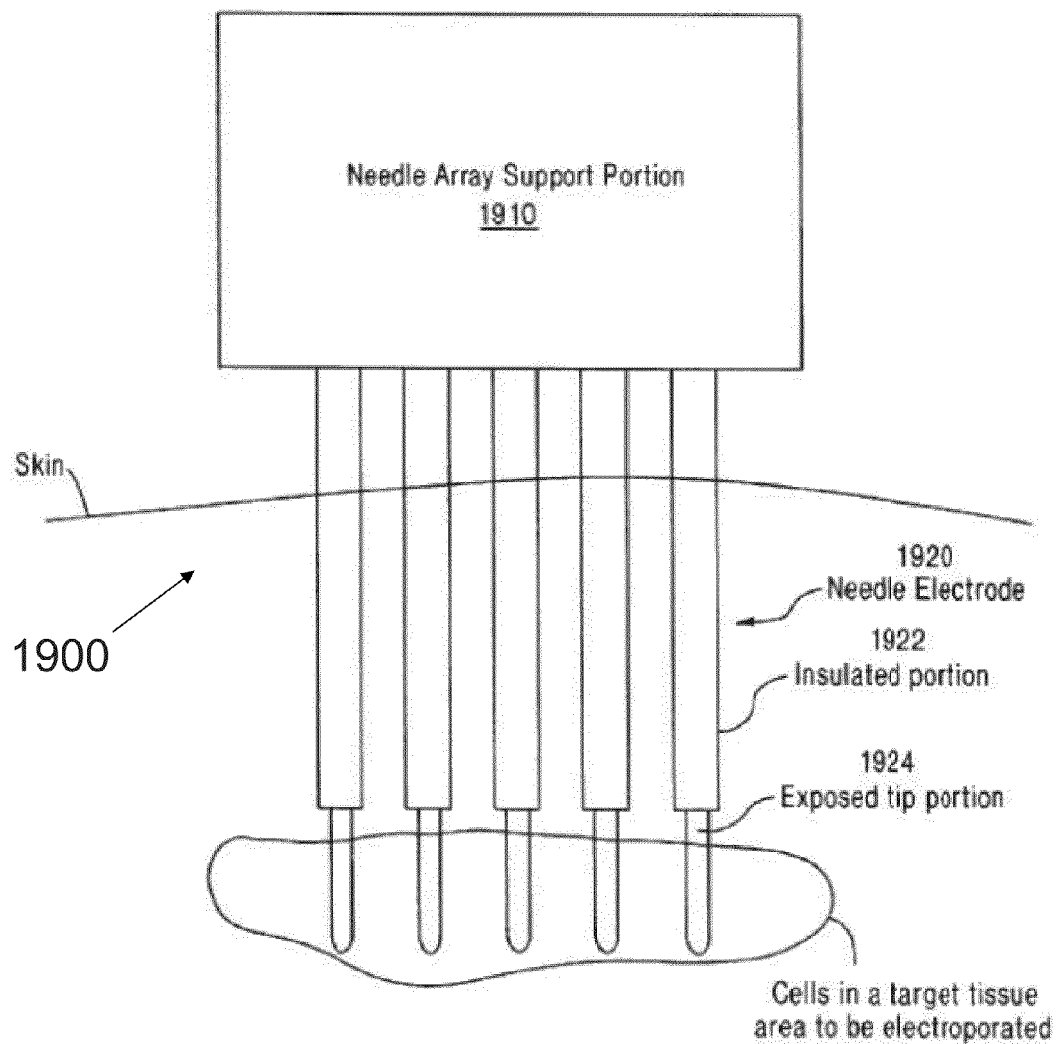
FIG. 8 is a schematic of one embodiment of an electrode needle array of the electroporation device of FIG. 2, illustrating partially insulated electrode needles.

FIG. 8 shows one embodiment of a partially insulated needle array 1900. A support portion 1910 is provided to hold multiple electrode needles 1920 in a predetermined array pattern. Each electrode needle 1920 has a base portion 1922 that is covered with a layer of electrically insulating material such as Teflon and a tip portion 1924 that is exposed. When electrical voltages are applied to the electrode needles 1920, the generated electrical fields in regions among and near the exposed tip portions 1924 are sufficiently strong to cause electroporation but the electrical fields in regions among and near the insulated base portions 1922 are either negligibly small or completely diminished so that electroporation cannot be effected due to the shielding of the insulation. Therefore, electroporation is localized or confined in regions where the exposed tip portions 1924 are positioned.

The lengths of the insulated base portion 1922 and the exposed tip portion 1924 may be predetermined or may be adjustable based on the location of a specific target area in a body part. In one implementation, each needle electrode may be pre-wrapped with a suitable insulating layer to cover most of the electrode needle with a minimal usable exposed tip portion. A user may adjust a desired amount of the exposed tip portion as needed in a treatment.

The partially insulated electrode needles shown in FIG. 8 can be used for both the fixed needle array as shown in FIG. 5 and the disposable needle array shown in FIGS. 4a and 4b.

3) Needle Array Addressing

The electroporation device 10 of FIG. 2 is designed to accommodate electrode applicators 22 having varying numbers of electrode needles 38, 46. Accordingly, an addressing scheme has been developed that, in the preferred embodiment, permits addressing up to 16 different needles, designated A through P, forming up to 9 square treatment zones and several types of enlarged treatment zones. A treatment zone comprises at least 4 needles in a configuration of opposing pairs that are addressed during a particular pulse. During a particular pulse, two of the needles of a treatment zone are of positive polarity and two are of negative polarity.

Figure 9:
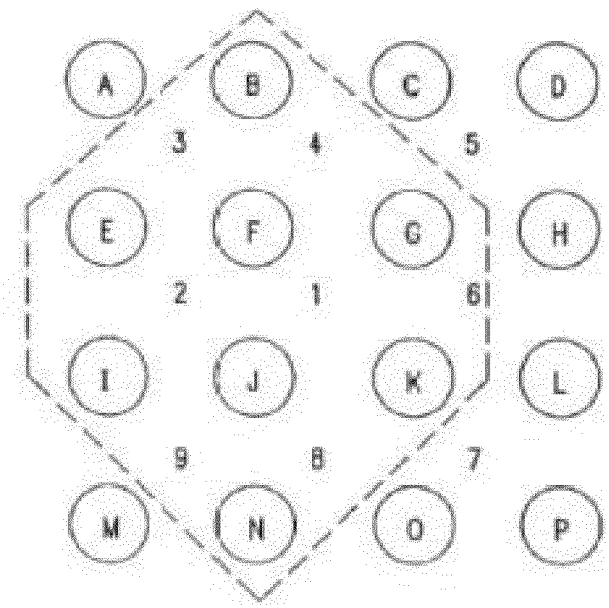
FIG. 9 is a schematic of a 4×4 mapping array for needles of the electroporation device of FIG. 2, illustrating 9 treatment zones.

FIG. 9 shows a preferred 4×4 mapping array for needles forming 9 square treatment zones numbered from the center and proceeding outward radially and then clockwise. In the preferred embodiment, this mapping array defines 4-needle, 6-needle, 8-needle, 9-needle, and 16-needle electrode configurations. A 4-needle electrode comprises needles placed in positions F, G, K, and J (treatment zone 1). A 9-needle electrode comprises needles placed in positions defining treatment zones 1-4. A 16-needle electrode comprises needles placed in positions defining treatment zones 1-9.

Figure 10A:
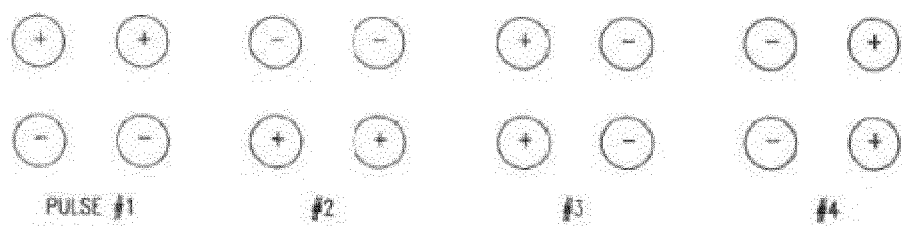
FIG. 10a is a schematic of a pulse sequence for a 2×2 treatment zone of the electroporation device of FIG. 2.

FIG. 10a shows a pulse switching sequence for a 2×2 treatment zone or mapping array in accordance with one embodiment of the invention. During any of four pulses comprising a cycle, opposing pairs of needles are respectively positively and negatively charged, as shown. Other patterns of such pairs are possible, such as clockwise or counterclockwise progression. For example, for a 9-needle electrode configuration, a preferred cycle comprises 16 pulses (4 treatment zones at 4 pulses each). For example, for a 16-needle electrode configuration, a preferred cycle comprises 36 pulses (9 treatment zones at 4 pulses each).

Figure 10B:
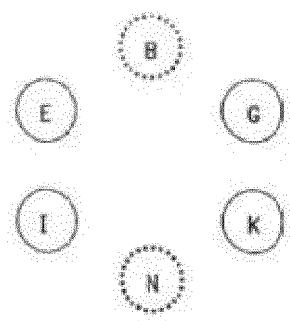
FIGS. 10b-10d illustrate a pulse sequence for a 6-needle array of the electroporation device of FIG. 2.
Figure 10C:
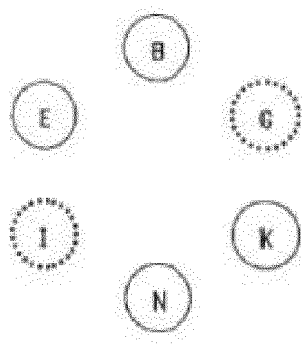
Figure 10D:
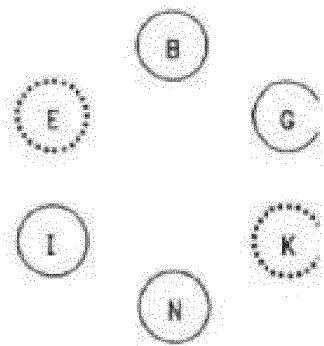

A 6-needle electrode can comprise a circular or hexagonal array as shown in FIGS. 10b-10d. Alternatively, a 6-needle electrode can be defined as a subset of a larger array, such as is shown in FIG. 9. For example, with reference to FIG. 9, a 6-needle electrode can be defined as a 2×3 rectangular array of needles placed in positions defining treatment zones 1-2 (or any other linear pair of treatment zones), or a hexagonal arrangement of needles B, G, K, N, I, E (or any other set of positions defining a hexagon) defining an enlarged treatment zone (shown in dotted outline in FIG. 9). Similarly, an 8-needle electrode can comprise an octagon, or a subset of the larger array shown in FIG. 9. For example, with reference to FIG. 9, an 8-needle electrode can be defined as a 2×4 array of needles placed in positions defining treatment zones 1, 2 and 6 (or any other linear triplet of treatment zones), or an octagonal arrangement of needles B, C, H, L, O, N, I, E (or any other set of positions defining an octagon) defining an enlarged treatment zone.

FIGS. 10b-10d show a hexagonal arrangement and one possible activation sequence. FIG. 10b shows a first sequence, in which needles G and K are positive and needles I and E are negative during a first pulse, and have reversed polarities during a next pulse; needles B and N, shown in dotted outline, are inactive. FIG. 10c shows a second sequence, in which needles K and N are positive and needles E and B are negative during a first pulse, and have reversed polarities during a next pulse; needles G and I are inactive. FIG. 10d shows a third sequence, in which needles N and I are positive and needles B and G are negative during a first pulse, and have reversed polarities during a next pulse; needles K and E are inactive. In some embodiments, a total of 6 pulses may be applied in a cycle of sequences. A similar activation sequence can be used for an octagonal arrangement, which may apply other numbers of pulses.

Regardless of physical configuration, the preferred embodiments of the invention may use at least two switched pairs of electrodes (for example, as shown in FIG. 10a) in order to achieve a relatively uniform electric field in tissue undergoing EPT. The electric field intensity should be of sufficient intensity to effect the process of electroporation, to allow incorporation of a treatment agent.

H) "Sweet Spot" Manipulation

The electroporation device 10 may produce a "sweet spot" during use. The "sweet spot" can be defined as the area in the tissue where the first electric signal 94 interferes with the second electric signal 110 to produce the resultant wave 130. In some embodiments, the electroporation device 10 is designed to move the "sweet spot" with respect to the needles 38, 46 of the electrode applicator 22. More specifically, the electroporation device 10 may adjust the amplitude, frequency, and pulse time of the signals being produced at each individual electrode needle 38, 46 to move, with respect to the electrode needles 38, 46, the exact location where the resultant wave 130 is produced in the tissue. As such, the device 10 is able to treat multiple areas of the tissue without the need to continuously move the applicator 22. Although a unipolar resultant result interference waveform can effectively target the sweet spot, a bipolar resultant interference waveform may more effectively target or move the sweet spot compared to a unipolar resultant interference waveform, depending on the usage requirements or preferences for the particular electroporation device 10.

II) THERAPEUTIC METHOD

The electroporation device 10 may be used in a therapeutic method. The therapeutic method of the invention includes electrotherapy, also referred to herein as electroporation therapy (EPT), for the delivery of an agent or molecule to a cell or tissue. The term "agent" or "molecule" as used herein refers to, for example, drugs (e.g., chemotherapeutic agents), nucleic acids (e.g., polynucleotides), peptides, and polypeptides, including antibodies. The term polynucleotides include DNA, cDNA, and RNA sequences. It should be understood that the electroporation of tissue can be performed in vitro, in vivo, or ex vivo. Electroporation can also be performed utilizing single cells, e.g., single cell suspensions, in vitro, or ex vivo in cell culture.

Drugs contemplated for use in the method of the invention are typically chemotherapeutic agents having an antitumor or cytotoxic effect. Such drugs or agents include bleomycin, neocarcinostatin, suramin, doxorubicin, carboplatin, taxol, mitomycin C, and cisplatin. Other chemotherapeutic agents will be known to those of ordinary skill in the art (see, for example, The Merck Index). In addition, "membrane-acting" agents are also included in the method of the invention. These agents may also be agents as listed above, or alternatively, agents which act primarily by damaging the cell membrane. Examples of membrane-acting agents include N-alkylmelamide and para-chloro mercury benzoate. The chemical composition of the agent will dictate the most appropriate time to administer the agent in relation to the administration of the electric pulse. For example, while not wanting to be bound by a particular theory, it is believed that a drug having a low isoelectric point (e.g., neocarcinostatin, IEP=3.78), would likely be more effective if administered post-electroporation in order to avoid electrostatic interaction of the highly charged drug within the field. Further, such drugs as bleomycin, which have a very negative log P, (P being the partition coefficient between octanol and water), are very large in size (MW=1400), and are hydrophilic, thereby associating closely with the lipid membrane, diffuse very slowly into a tumor cell and are typically administered prior to or substantially simultaneous with the electric pulse. In addition, certain agents may require modification in order to enter the cell allow more efficiently. For example, an agent such as taxol can be modified to increase solubility in water which would allow it to enter the cell more efficiently. Electroporation facilitates entry of bleomycin or other similar drugs into the tumor cell by creating pores in the cell membrane.

In one embodiment, the invention provides a method of electroporating cells using the electroporation device 10, comprising administering selected molecules into the cells within the cover area 220, contacting the cells with the electrodes 34, 42, and the electroporating signals 94, 110. In some embodiments, the cover area 220 of the electrodes 34, 42 may be adjusted before contacting the cells with the electrodes 34, 42. In further embodiments, the electric field associated with the electroporating signals 94, 110 may be maintained within a predetermined range so as to substantially prevent permanent damage in the cells within the cover area 220, and to minimize pain.

In another embodiment, the invention provides a method for the therapeutic application of electroporation to a tissue of a subject for introducing molecules into cells therein, comprising providing an array of electrodes, at least one of the electrodes having a needle configuration for penetrating tissue; inserting the needle electrode into selected tissue for introducing molecules into the tissue; positioning a second electrode of the array of electrodes in conductive relation to the selected tissue; applying a first electric signal to the first electrode and applying a second electric signal to the second electrode such that a resultant electrical signal or wave is formed in the tissue from the wave interference between the first wave and the second wave. The resultant wave has a beat frequency sufficient to cause electroporation in the cell wall, and the embedded frequency is sufficient to minimize pain.

In addition to minimizing pain and tissue damage, the method of the invention may increase the uptake of the agent by cells relative to a method that does not employ EPT. Uptake or introduction of the agent to the cells may be increased by about 0.5-fold to about 50-fold, about 0.5-fold to about 45-fold, about 0.5-fold to about 40-fold, about 0.5-fold to about 35-fold, about 0.5-fold to about 30-fold, about 0.5-fold to about 25-fold, about 1-fold to about 50-fold, about 1.5-fold to about 50-fold, about 2-fold to about 50-fold, about 2.5-fold to about 50-fold, or about 3-fold to about 50-fold. Uptake of the agent by the cells may be increased by 0.5-fold to about 6-fold, about 0.75-fold to about 6-fold, about 1-fold to about 6-fold, about 1.25-fold to about 6-fold, about 1.5-fold to about 6-fold, about 1.75-fold to about 6-fold, about 2-fold to about 6-fold, about 2.25-fold to about 6-fold, about 2.5-fold to about 6-fold, about 2.75-fold to about 6-fold, about 3-fold to about 6-fold, about 3.25-fold to about 6-fold, about 0.5-fold to about 5.75-fold, about 0.5-fold to about 5.5-fold, about 0.5-fold to about 5.25-fold, about 0.5-fold to about 5-fold, about 0.5-fold to about 4.75-fold, about 0.5-fold to about 4.5-fold, about 0.5-fold to about 4.25-fold, about 0.5-fold to about 4-fold, or about 0.5-fold to about 3.75-fold. Uptake of the agent by the cells may also be increased by about 0.75-fold to about 5.75-fold, about 1-fold to about 5.5-fold, about 1.25-fold to about 5.25-fold, about 1.5-fold to about 5-fold, about 1.75-fold to about 4.75-fold, about 2-fold to about 4.5-fold, about 2.25-fold to about 4.25-fold, about 2.5-fold to about 4-fold or about 2.75-fold to about 3.75-fold.

Uptake of the agent by the cells may be increased by about 18-fold to about 30-fold, about 18-fold to about 29-fold, about 18-fold to about 28-fold, about 18-fold to about 27-fold, about 18-fold to about 26-fold, about 18-fold to about 24-fold, about 19-fold to about 30-fold, about 20-fold to about 30-fold, about 21-fold to about 30-fold, about 22-fold to about 30-fold or about 23-fold to about 30-fold. Uptake of the agent by the cells may also be increased by about 19-fold to about 29-fold, about 20-fold to about 28-fold, about 21-fold to about 27-fold, about 22-fold to about 26-fold, about 23-fold to about 25-fold, or about 23-fold to about 24-fold. Uptake of the agent by the cells may be increased by about 18-fold, about 19-fold, about 20-fold, about 21-fold, about 22-fold, about 23-fold, about 24-fold, about 25-fold, about 26-fold, about 27-fold, about 28-fold, about 29-fold, or about 30-fold.

In another embodiment, uptake or introduction of the agent to the cells may be increased by about 50% to about 5000%, about 50% to about 4500%, about 50% to about 4000%, about 50% to about 3500%, about 50% to about 3000%, about 50% to about 2500%, about 100% to about 5000%, about 150% to about 5000%, about 200% to about 5000%, about 250% to about 5000%, or about 300% to about 5000%. Uptake of the agent by the cells may be increased by about 50% to about 600%, about 75% to about 600%, about 100% to about 600%, about 125% to about 600%, about 150% to about 600%, about 175% to about 600%, about 200% to about 600%, about 225% to about 600%, about 250% to about 600%, about 275% to about 600%, about 300% to about 600%, about 325% to about 600%, about 50% to about 575%, about 50% to about 550%, about 50% to about 525%, about 50% to about 500%, about 50% to about 475%, about 50% to about 450%, about 50% to about 425%, about 50% to about 400%, or about 50% to about 375%. Uptake of the agent by the cells may also be increased by about 75% to about 575%, about 100% to about 550%, about 125% to about 525%, about 150% to about 500%, about 175% to about 475%, about 200% to about 450%, about 225% to about 425%, about 250% to about 400%, or about 275% to about 375%. Uptake of the agent by the cells may be increased by about 345%, about 346%, about 347%, about 348%, about 349%, about 350%, about 351%, about 352%, about 353%, about 354%, about 355%, about 356%, about 357%, about 358%, about 359%, about 360%, about 361%, about 363%, about 364%, about 365%, about 366%, about 367%, about 368%, about 369%, about 370%, about 371%, about 372%, about 373%, about 374%, about 375%, about 376%, about 377%, about 378%, about 379%, or about 380%.

Uptake of the agent by the cells may also be increased by about 1800% to about 3000%, about 1800% to about 2900%, about 1800% to about 2800%, about 1800% to about 2700%, about 1800% to about 2600%, about 1800% to about 2500%, about 1800% to about 2400%, about 1900% to about 3000%, about 2000% to about 3000%, about 2100% to about 3000%, about 2200% to about 3000%, or about 2300% to about 3000%. Uptake of the agent by the cells may be increased by about 1850% to about 2950%, about 1900% to about 2900%, about 1950% to about 2850%, about 2000% to about 2800%, about 2050% to about 2750%, about 2100% to about 2700%, about 2150% to about 2650%, about 2200% to about 2600%, about 2250% to about 2550%, about 2300% to about 2500%, or about 2350% to about 2450%. Uptake of the agent by the cells may be increased by about 2300%, about 2310%, about 2320%, about 2330%, about 2340%, about 2350%, about 2360%, about 2361%, about 2362%, about 2363%, about 2364%, about 2365%, about 2366%, about 2367%, about 2368%, about 2369%, about 2370%, about 2371%, about 2372%, about 2373%, about 2374%, about 2375%, about 2376%, about 2377%, about 2378%, about 2379%, about 2380%, about 2381%, about 2382%, about 2383%, about 2384%, about 2385%, about 2386%, about 2387%, about 2388%, about 2389% or about 2390%.

Accordingly, the method of the invention minimizes the pain experienced by the subject by decreasing impedance due to cell structure (e.g., skin) while increasing the efficiency of introducing the agent into a cell(s). The method of the invention advantageously provides effective delivery of the agent to within the cells, but unlike other electrotherapy methods, minimizes (or reduces) the pain experienced by the subject due to impedance.

It may be desirable to modulate the expression of a gene in a cell by the introduction of a molecule by the method of the invention. The term "modulate" envisions for example the suppression of expression of a gene when it is over-expressed, or augmentation of expression when it is under-expressed. Where a cell proliferative disorder is associated with the expression of a gene, nucleic acid sequences that interfere with the gene's expression at the translational level can be used. This approach utilizes, for example, antisense nucleic acid, ribozymes, or triplex agents to block transcription or translation of a specific mRNA, either by masking that mRNA with an antisense nucleic acid or triplex agent, or by cleaving it with a ribozyme.

It is to be understood that the above described treatment may be utilized on various forms of solid cancer types, such as, but not limited to, sarcomas, carcinomas, and lymphomas. Solid tumors may be located throughout the body such as in the neck, lungs, skin, brain, prostate, liver, pancreatic, gall bladder, stomach, and lymph nodes. These tumors may further metastasize to other locations throughout the body. The electroporation device 10 can be used to introduce agents such as bleomycin to kill the tumor by necrosis and further stimulate the immune system to prevent metastasis.

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher, et al., Antisense Res. and Dev., 1(3):227, 1991; Helene, C., Anticancer Drug Design, 6(6): 569, 1991).

Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes, namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11-18 bases in length. The longer the recognition sequence, the greater the likelihood that the sequence will occur exclusively in the target mRNA species. Consequently, 18-based recognition sequences are preferable to shorter recognition sequences. Therefore, "hammerhead"-type ribozymes are preferable to tetrahymena-type ribozymes for inactivating a specific mRNA species.

The invention also provides gene therapy for the treatment of cell proliferative or immunologic disorders mediated by a particular gene or absence thereof. Such therapy would achieve its therapeutic effect by introduction of a specific sense or antisense polynucleotide into cells having the disorder. Delivery of polynucleotides can be achieved using a recombinant expression vector such as a chimeric virus, or the polynucleotide can be delivered as "naked" DNA for example.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). When the subject is a human, a vector such as the gibbon ape leukemia virus (GaLV) can be utilized. A number of additional retroviral vectors can incorporate multiple genes. All of these vectors can transfer or incorporate a gene for a selectable marker so that transduced cells can be identified and generated.

Therapeutic peptides or polypeptides may also be included in the therapeutic method of the invention. For example, immunomodulatory agents and other biological response modifiers can be administered for incorporation by a cell. The term "biological response modifiers" is meant to encompass substances which are involved in modifying the immune response. Examples of immune response modifiers include such compounds as lymphokines Lymphokines include tumor necrosis factor, interleukins 1, 2, and 3, lymphotoxin, macrophage activating factor, migration inhibition factor, colony stimulating factor, and alpha-interferon, beta-interferon, and gamma-interferon and their subtypes.

Also included are polynucleotides which encode metabolic enzymes and proteins, including antiangiogenesis compounds, e.g., Factor VIII or Factor IX. The macromolecule of the invention also includes antibody molecules. The term "antibody" as used herein is meant to include intact molecules as well as fragments thereof, such as Fab and F(ab')$_2$.

Administration of a drug, polynucleotide or polypeptide, in the method of the invention can be, for example, parenterally by injection, rapid infusion, nasopharyngeal absorption, dermal absorption, and orally. In the case of a tumor, for example, a chemotherapeutic or other agent can be administered locally, systemically, or directly injected into the tumor. When a drug, for example, is administered directly into the tumor, it is advantageous to inject the drug in a "fanning" manner. The term "fanning" refers to administering the drug by changing the direction of the needle as the drug is being injected or by multiple injections in multiple directions like opening up of a hand fan, rather than as a bolus, in order to provide a greater distribution of drug throughout the tumor. As compared with a volume that is typically used in the art, it is desirable to increase the volume of the drug-containing solution, when the drug is administered (e.g., injected) intratumorally, in order to ensure adequate distribution of the drug throughout the tumor. For example, in the EXAMPLES using mice herein, one of skill in the art typically injects 50 µl of drug-containing solution, however, the results are greatly improved by increasing the volume to 150 µl. In human clinical studies, approximately 20 ml would be injected to ensure adequate perfusion of the tumor. Preferably, the injection should be done very slowly all around the base and by fanning. Although the interstitial pressure is very high at the center of the tumor, it is also a region where very often the tumor is necrotic.

Preferably, the molecule is administered substantially contemporaneously with the electroporation treatment. The term "substantially contemporaneously" means that the molecule and the electroporation treatment are administered reasonably close together with respect to time, i.e., before the effect of the electrical pulses on the cells diminishes. The administration of the molecule or therapeutic agent depends upon such factors as, for example, the nature of the tumor, the condition of the patient, the size and chemical characteristics of the molecule, and the half-life of the molecule.

Preparations for parenteral administration include sterile, aqueous, or non-aqueous solutions, suspensions, and emulsions. Examples of non-aqueous solvents are propylene glycol, polyethylene glycol, vegetable oils such as olive oil, and injectable organic esters such as ethyl oleate. Besides the inert diluents, such compositions can also include adjuvants, wetting agents, emulsifying, and suspending agents. Further, vasoconstrictor agents can be used to keep the therapeutic agent localized prior to pulsing.

Any cell can be treated by the method of the invention. The illustrative examples provided herein demonstrate the use of the method of the invention for the treatment of tumor cells, e.g., pancreas, lung, head and neck, cutaneous and subcutaneous cancers. Other cell proliferative disorders are amenable to treatment by the electroporation method of the invention. The term "cell proliferative disorder" denotes malignant as well as non-malignant cell populations which often appear to differ from the surrounding tissue both morphologically and genotypically. Malignant cells (i.e., tumors or cancer) develop as a result of a multi-step process. The method of the invention is useful in treating malignancies or other disorders of the various organ systems, particularly, for example, cells in the pancreas, head and neck (e.g., larynx, nasopharynx, oropharynx, hypopharynx, lip, throat,) and lung, and also including cells of heart, kidney, muscle, breast, colon, prostate, thymus, testis, and ovary. Further, malignancies of the skin, such as basal cell carcinoma or melanoma may also be treated by the therapeutic method of the invention (see Example 2). Preferably the subject is human; however, it should be understood that the invention is also useful for veterinary uses in non-human animals or mammals.

In yet another embodiment, the invention provides a method for the therapeutic application of electroporation to a tissue of a subject for damaging or killing cells therein while minimizing the amount of pain experienced by the patient. The method includes providing an array of electrodes; positioning a second electrode of the array of electrodes in conductive relation to the selected tissue; and applying a first electric signal to the first electrode and applying a second electric signal to the second electrode such that a resultant electrical signal or wave is formed from the wave interference between the first signal and the second. The method may utilize a low voltage and a long pulse length, e.g., a nominal electric field from about 25 V/cm to 75 V/cm and pulse length from about 5 µsec to 99 msec.

The following examples are intended to illustrate but not limit the invention. While they are typical of those that might be used, other procedures known to those skilled in the art may alternatively be used.

III) EXAMPLES

Example 1

Interference Electroporation Treatment In Vitro

Materials and Methods

Plasmid.

The plasmid gWiz-Luc, which encoded luciferase, was acquired from Aldevron (Fargo, N. Dak.).

Electroporation.

B16 F10 cells (2.5×10$^6$ cells/mL) were prepared in complete medium (i.e., Mcoy's 5A medium with 10% Fetal Bovine Serum (FBS)). Cells were split into two groups, Group 1 and Group 2. Group 1 cells were mixed with DNA, but received no interference electroporation (IEP) treatment. Specifically, 1 mL of cell suspension was transferred to a cuvette and 50 µL gWiz-Luc (2 mg/mL) was added to this cuvette to arrive at a final concentration of 100 µg/mL of DNA. The cells and DNA were mixed by pipette before placement into a cuvette holder. The cells received no IEP treatment and the cell suspension was subsequently transferred to a 6-well plate. The cells were incubated at 37 degrees Celsius, 5% CO$_2$ before imaging as described below.

Group 2 cells were mixed with DNA and then received IEP treatment. Specifically, two cuvettes were prepared, in which each cuvette received 1 mL of cell suspension and 50 µL gWiz-Luc (2 mg/mL) to arrive at a final concentration of 100 µg/mL of DNA. A pipette was used to mix the cell suspension and DNA before placement of each cuvette into a cuvette holder. The parameters for IEP were 650V/cm each channel×2 channels, 100 µs, 1 KHz, 6 pulses. After IEP, 140 µL of cell suspension was transferred from each cuvette into a respective well of a E-well plate. Each well contained 2 mL complete medium. This was done in triplicate for each cuvette (i.e., 3 wells for each cuvette). The cells were incubated at 37 degrees Celsius, 5% CO$_2$ before imaging as described below.

Cell Imaging.

24 hours (hr) after electroporation, medium was removed from each well of the 6-well plates and 300 µL pre-warmed medium containing D-luciferin (250 µg/ml, Goldbio, St. Louis, Mo., USA) was added to each well. Cells were then incubated at 37 degrees Celsius for 5 minutes (min) before imaging. Imaging was done with an IVIS Spectrum system (Caliper Life Sciences, Hopkinton, Mass., USA) and assessment of photonic emissions from the cells was performed about 8 min to about 10 min after incubation of the cells with D-luciferin.

Results

To determine if interference electroporation (IEP) could increase the efficiency of molecule uptake by cells, an in vitro system was utilized, in which cells were split into two different treatment groups. The two treatment groups were as follows: Group 1 was cells mixed with DNA, but receiving no IEP treatment; and Group 2 was cells mixed with DNA and receiving IEP treatment. The DNA used was a plasmid that encoded luciferase and DNA uptake was indirectly measured by luciferase activity. Luciferase acts upon its substrate D-luciferin to cause the emission of light or photons.

Figure 14:
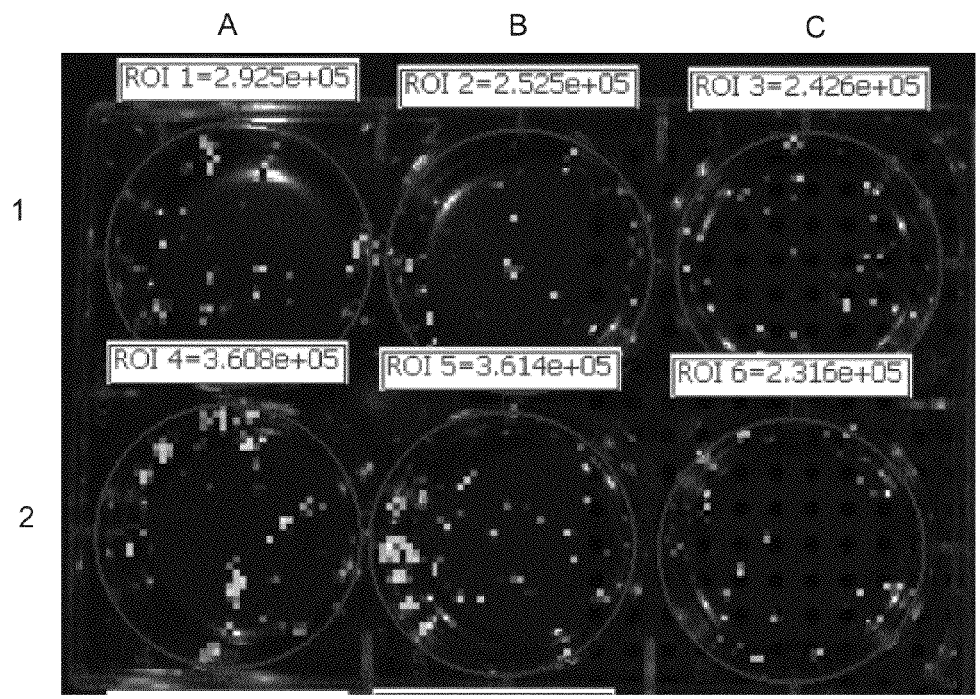
FIG. 14 shows photonic emission at 24 hours for cells mixed with DNA encoding luciferase.
Figure 15:
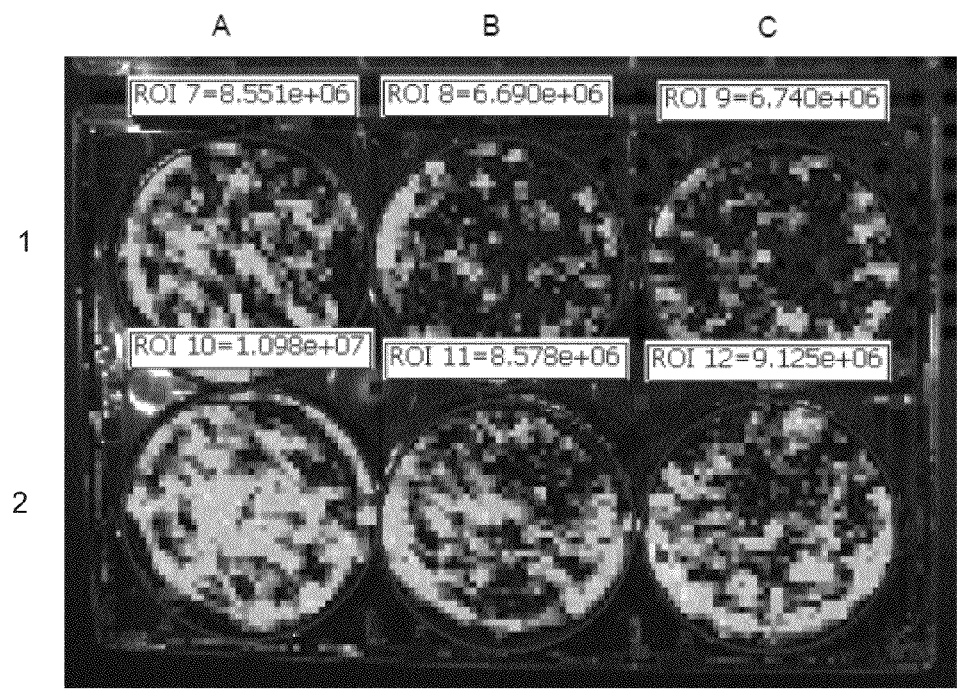
FIG. 15 shows photonic emission at 24 hours for cells mixed with DNA encoding luciferase and then treated with interference electroporation.
Figure 16:
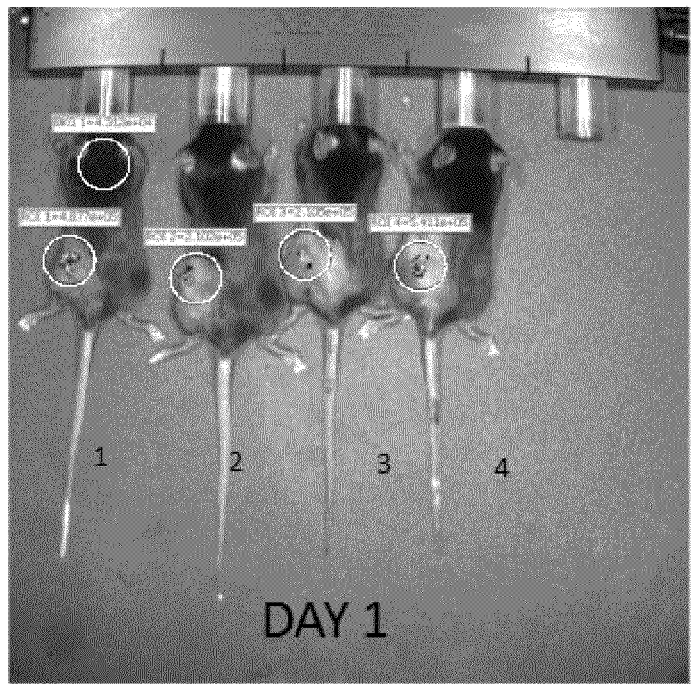
FIG. 16 shows photonic emission of mice at day 1 following injection with plasmid DNA.
Figure 17:
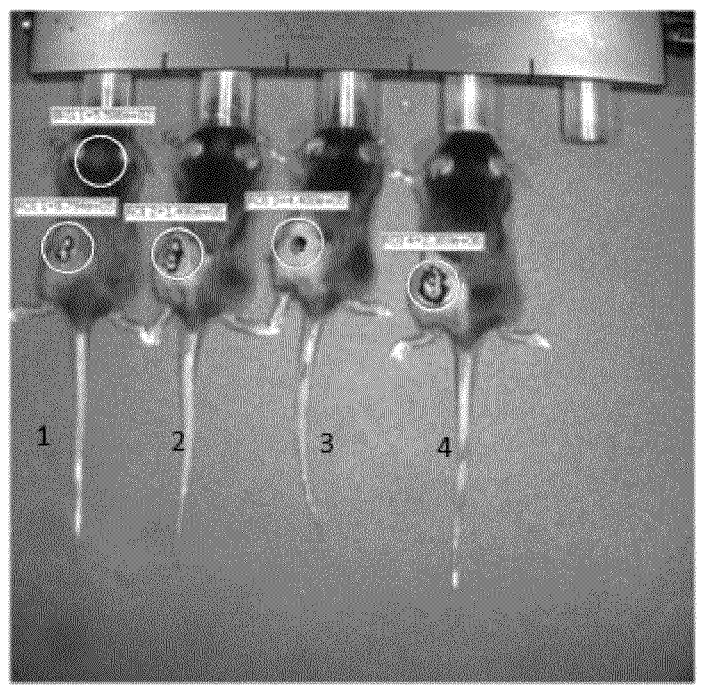
FIG. 17 shows photonic emission of mice at day 1 following injection with plasmid DNA and treatment with interference electroporation.
Figure 18:
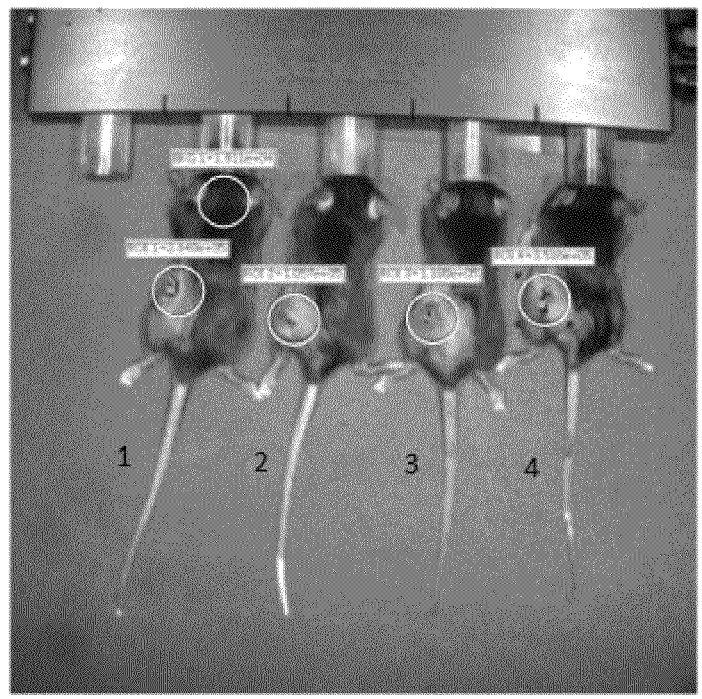
FIG. 18 shows photonic emission of mice at day 2 following injection with plasmid DNA.
Figure 19:
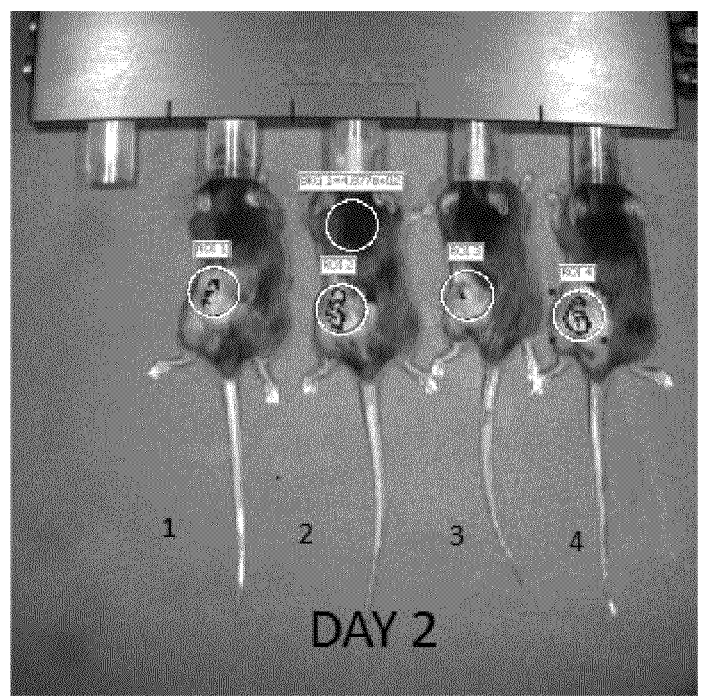
FIG. 19 shows photonic emission of mice at day 2 following injection with plasmid DNA and treatment with interference electroporation.
Figure 20:
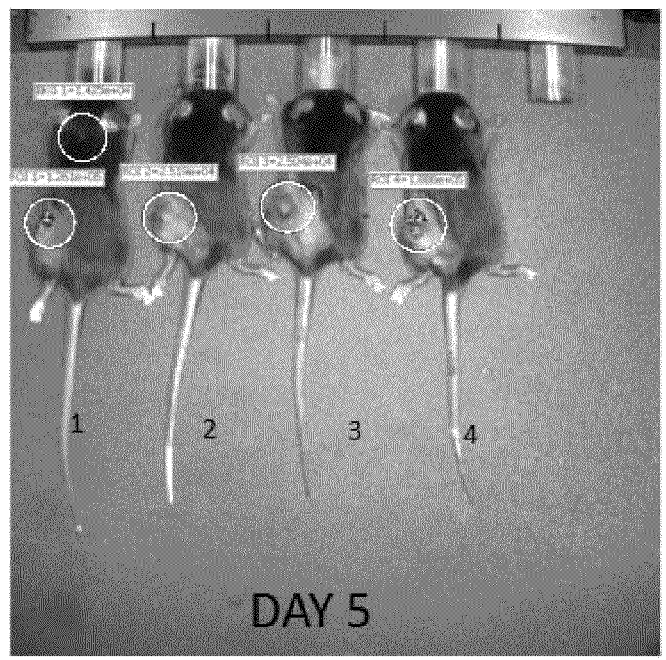
FIG. 20 shows photonic emission of mice at day 5 following injection with plasmid DNA.
Figure 21:
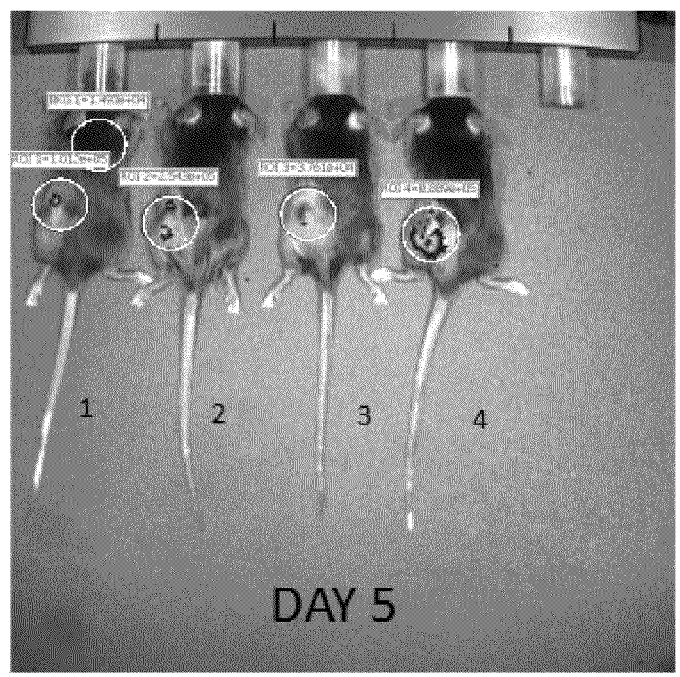
FIG. 21 shows photonic emission of mice at day 5 following injection with plasmid DNA and treatment with interference electroporation.
Figure 22:
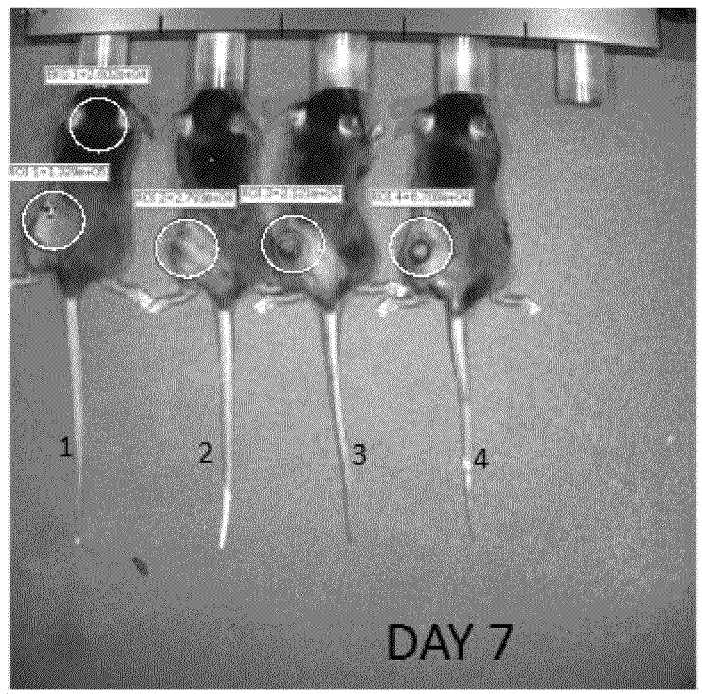
FIG. 22 shows photonic emission of mice at day 7 following injection with plasmid DNA.
Figure 23:
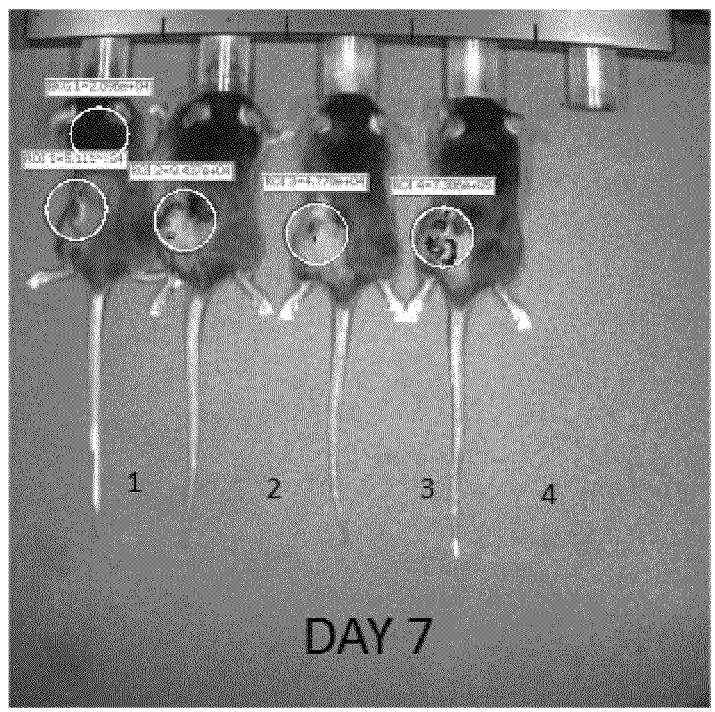
FIG. 23 shows photonic emission of mice at day 7 following injection with plasmid DNA and treatment with interference electroporation.

FIGS. 14 and 15 show the captured images of photonic emission ($p/sec/cm^2/sr$) from Groups 1 and 2, respectively, 24 hours after electroporation. The measurement for each well and the average emission for Groups 1 and 2 are shown in Table 1. For each of Groups 1 and 2, the average emission was calculated by averaging the measurements from the six wells depicted in FIGS. 14 and 15, respectively. For FIG. 15, each row of three wells corresponded to one of the two cuvettes described above that received IEP treatment.

TABLE 1

| | Measured Photon Emission ($p/sec/cm^2/sr$) | | | | | | |
|---|---|---|---|---|---|---|---|
| | Well 1A | Well 1B | Well 1C | Well 2A | Well 2B | Well 2C | Average |
| Group 1 | 2.93E+05 | 2.53E+05 | 2.43E+05 | 3.61E+05 | 3.61E+05 | 2.32E+05 | 2.90E+05 |
| Group 2 | 8.55E+06 | 6.69E+06 | 6.74E+06 | 1.10E+07 | 8.58E+06 | 9.13E+06 | 8.44E+06 |

As shown in FIGS. 14 and 15 and Table 1, IEP treatment increased photonic emission by 2374% as compared to cells that did not receive IEP treatment. These data indicated that IEP treatment significantly increased DNA uptake by cells. Regular electroporation worked at least as well as IEP (data not shown).

Example 2

Interference Electroporation Treatment In Vivo

Materials and Methods

Plasmid.

The plasmid gWiz-Luc, which encoded luciferase, was obtained from Aldevron (Fargo, N. Dak.). The gWiz-Luc preparation had endotoxin levels less than 100 EU/mg.

Cells.

B16.F10 melanoma cells were maintained in McCoy's 5A media (Mediatech, Manassas, Va.) supplemented with 10% fetal bovine serum (Life Technologies, Grand Island, N.Y.) and 1% Gentamycin at 37 degrees Celsius and 5% $CO_2$ humidified air.

Mice.

Female C57BL/6J mice (6-8 weeks old) were purchased from Jackson Laboratories (Bar Harbour, Me.).

Tumor Establishment.

50 µL of B16.F10 melanoma cells ($1\times10^6$ cells) were introduced by subcutaneous (s.c.) injection into the shaved left flank of the C57BL/6J mouse in order to establish the tumor. Each mouse was monitored closely for tumor development and tumor volume was measured using digital calipers. Tumor volume was calculated by using the formula for the volume of an ellipsoid: $v=\pi ab^2/6$, where a is the long diameter and b is the short diameter. Tumors were allowed to grow to a diameter of 3 millimeters (mm) to 5 mm (about 5 days after s.c. injection) before delivery of plasmid DNA as described below.

Electroporation.

A tumor was established in each mouse as described above and after the tumor reached a diameter of 3 mm to 5 mm, 50 µg of plasmid DNA (2 mg/mL) was injected directly into the tumor using a syringe with a 25 gauge needle. The electrode was placed around the tumor and pulses were applied using an interference electroporation (IEP) protocol. The IEP protocol employed a 4-needle electrode with the following parameters: (1) 650 V/channel, 100 µs, 6 pulses, 900 µs gap.

Imaging.

Each mouse was anesthetized and D-Luciferin was injected into the tumor. Imaging was done with an IVIS Spectrum system (Caliper Life Sciences, Hopkinton, Mass., USA). Photonic emissions from the tumor of each mouse was imaged at day 1, day 2, day 5, and day 7 after electroporation treatment. A portion of the mouse that did not contain the tumor was also imaged and served as a control for background photonic emissions.

Results

The data above demonstrated that interference electroporation (IEP) increased the efficiency of DNA uptake by cells in vitro. To further examine the capabilities of IEP, DNA uptake in vivo was examined. In particular, tumors were established in two groups of mice and plasmid DNA was administered to each tumor by injection. Group 1 received no IEP treatment and contained four mice. Group 2 also contained four mice and received IEP treatment with the parameters: 650 V/channel, 100 µs, 6 pulses, 900 µs gap. Each group of mice was imaged at day 1, day 2, day 5, and day 7 after DNA administration to measure photonic emissions from the tumors.

FIGS. 16, 18, 20, and 22 show the captured images of the photonic emissions ($p/sec/cm^2/sr$) from the tumors of Group 1 mice at day 1, day 2, day 5, and day 7, respectively. FIGS. 17, 19, 21, and 23 show the captured images of the photonic emissions from the tumors of Group 2 mice at day 1, day 2, day 5, and day 7, respectively. The solid circle on the hind region of each mouse indicated the area imaged for the tumor. An additional area was imaged on one mouse in each of Group 1 and 2 to provide a control for background photonic emission (see solid circle on the head region of the mouse). Tables 2-5 list the measurements obtained for each mouse on day 1, day 2, day 5, and day 7, respectively, for Groups 1 and 2. The average photonic emission in Tables 2-5 is an average of the photonic emission of the four mice in each of Groups 1 and 2.

TABLE 2

Measured Photon Emission (p/sec/cm$^2$/sr) on Day 1

|  | Mouse 1 | Mouse 2 | Mouse 3 | Mouse 4 | Average |
|---|---|---|---|---|---|
| Group 1 | 4.88E+05 | 2.10E+05 | 2.11E+05 | 5.41E+05 | 3.62E+05 |
| Group 2 | 8.79E+05 | 1.49E+06 | 4.41E+05 | 2.37E+06 | 1.29E+06 |

TABLE 3

Measured Photon Emission (p/sec/cm$^2$/sr) on Day 2

|  | Mouse 1 | Mouse 2 | Mouse 3 | Mouse 4 | Average |
|---|---|---|---|---|---|
| Group 1 | 2.64E+05 | 1.06E+05 | 1.18E+05 | 3.52E+05 | 2.10E+05 |
| Group 2 | 4.51E+05 | 1.18E+06 | 9.55E+04 | 1.31E+06 | 7.59E+05 |

TABLE 4

Measured Photon Emission (p/sec/cm$^2$/sr) on Day 5

|  | Mouse 1 | Mouse 2 | Mouse 3 | Mouse 4 | Average |
|---|---|---|---|---|---|
| Group 1 | 1.26E+05 | 2.52E+04 | 2.50E+04 | 1.89E+05 | 9.12E+04 |
| Group 2 | 1.01E+05 | 2.54E+05 | 3.76E+04 | 8.89E+05 | 3.21E+05 |

TABLE 5

Measured Photon Emission (p/sec/cm$^2$/sr) on Day 7

|  | Mouse 1 | Mouse 2 | Mouse 3 | Mouse 4 | Average |
|---|---|---|---|---|---|
| Group 1 | 1.33E+05 | 2.79E+04 | 2.12E+04 | 6.71E+04 | 6.23E+04 |
| Group 2 | 5.11E+04 | 9.44E+04 | 4.78E+04 | 7.39E+05 | 2.33E+05 |

Figure 24:
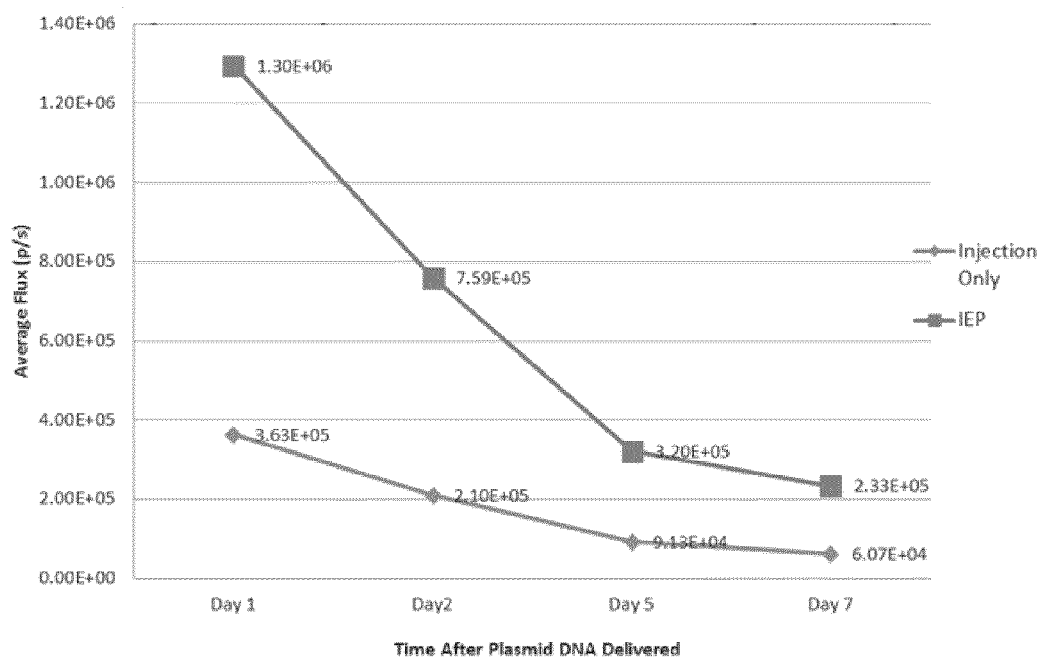
FIG. 24 is a graph plotting time after plasmid DNA delivery and average photon emission.

FIG. 24 shows a comparison of the average photonic emission for Groups 1 and 2 at day 1, day 2, day 3, and day 4. These data indicated that at each day, IEP treatment increased photonic emission from the tumors as compared to mice that did not receive IEP treatment. Particularly, IEP treatment increased photonic emission by 357%, 361%, 351%, and 374% on day 1, day 2, day 5, and day 7, respectively. Accordingly, these dated indicated that IEP treatment significantly increased DNA uptake by targeted cells (i.e., the tumor cells) in an animal. Regular electroporation worked at least as well as IEP (data not shown).

Example 3

Interference Electroporation Treatment does not Damage Tissue

Materials and Methods

Plasmid.

The plasmid gWiz-GFP, which encoded green fluorescent protein (GFP), was obtained from Aldevron (Fargo, N. Dak.). The gWiz-GFP preparation had endotoxin levels less than 100 EU/mg.

Cells.

B16.F10 melanoma cells were maintained in McCoy's 5A media (Mediatech, Manassas, Va.) supplemented with 10% fetal bovine serum (Life Technologies, Grand Island, N.Y.) and 1% Gentamycin at 37 degrees Celsius and 5% $CO_2$ humidified air.

Mice.

Female C57BL/6J mice (6-8 weeks old) were purchased from Jackson Laboratories (Bar Harbour, Me.).

Tumor Establishment.

50 µL of B16.F10 melanoma cells (1×10$^6$ cells) were introduced by subcutaneous (s.c.) injection into the shaved left flank of the C57BL/6J mouse in order to establish the tumor. Each mouse was monitored closely for tumor development and tumor volume was measured using digital calipers. Tumor volume was calculated by using the formula for the volume of an ellipsoid: $v=\pi ab^2/6$, where a is the long diameter and b is the short diameter. Tumors were allowed to grow to a diameter of 3 millimeters (mm) to 5 mm (about 5 days after s.c. injection) before delivery of plasmid DNA as described below.

Electroporation.

A tumor was established in each mouse as described above and after the tumor reached a diameter of 3 mm to 5 mm, 50 µg of plasmid DNA (2 mg/mL) was injected directly into the tumor using a syringe with a 25 gauge needle. The electrode was placed around the tumor and pulses were applied using an interference electroporation (IEP) protocol. The IEP protocol employed a 4-needle electrode with the following parameters: 650 V/channel, 100 µs, 6 pulses, 900 µs gap.

Staining.

Tumor sections were stained with hematoxylin and eosin (H&E) stain.

Results

The above data demonstrated that IEP increased the uptake of DNA by cells both in vitro (i.e., tissue culture) and in vivo (i.e., in established tumors in mice). The effect of IEP on cell biology was further examined by H&E staining of tumor sections after electroporation. In particular, the staining was utilized to determine if IEP caused tissue damage.

Tumors were established in two groups of mice and plasmid DNA was administered to each tumor by injection. Group 1 received no IEP treatment. Group 2 received IEP after injection. After 7 days, mice were sacrificed and the respective tumors were sectioned for H&E staining Representative staining for Groups 1 and 2 is shown in FIGS. 25a and 25b, respectively.

Figures 25A, 25B:
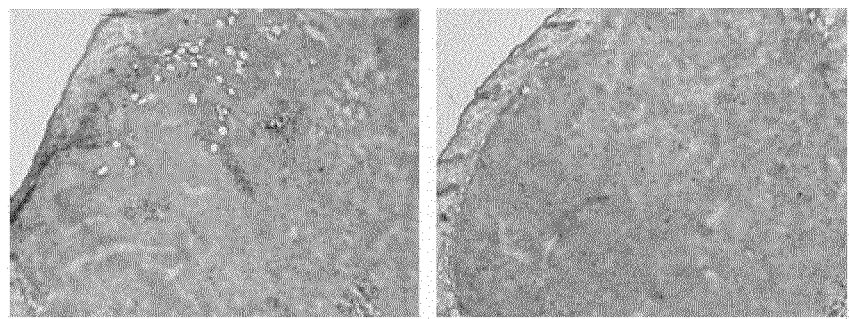
FIG. 25 shows representative hematoxylin and eosin (H&E) staining of tissue sections from mice (a) injected with plasmid DNA; and (b) injected with plasmid DNA and receiving interference electroporation treatment.

As seen in FIGS. 25a and 25b, similar cell morphology was observed in the stained tumor tissue sections from Groups 1 and 2. These data indicated that tissue receiving IEP treatment was not damaged by the electrical pulses from the IEP treatment.

Example 4

EPT for Treatment of Tumors In Vivo

A single treatment procedure will involve an injection of bleomycin (0.5 units in 0.15 ml saline) intratumorally, using fanning, followed by application of six electrical pulses of the first electrical signal and the second electrical signal, simultaneously, using needle array electrodes as described in the present application, arranged along the circumference of a circle 1 cm in diameter.

The needle arrays of variable diameters (e.g., 0.5 cm, 0.75 cm and 1.5 cm) can also be used to accommodate tumors of various sizes. Stoppers of various heights can be inserted at the center of the array to make the penetration depth of the needles into the tumor variable. A built-in mechanism will allow switching of electrodes for maximum coverage of the tumor by the pulsed field. The electrical parameters will be: 780 V/cm center field strength and 6×99 µs pulses spaced at 1-second intervals.

Example 5

Clinical Trials for Basal Cell Carcinomas and Melanomas

The effectiveness of bleomycin-EPT on tumors will be assessed similar to Example 1.

Example 6

EPT for Head and Neck Cancers

A single-center feasibility clinical study will be conducted in which the efficacy of the EPT procedure in combination with intralesional bleomycin will be compared to that for traditional surgery, radiation, and/or systemic chemotherapy. Approximately 50 study subjects will be enrolled in the study. All study subjects will be assessed prior to treatment by examination and biopsy. Patients will be treated with bleomycin intratumoral injection and needle arrays of different diameters with six needles. The voltage will be set to achieve a nominal electric field strength of 1300 V/cm (the needle array diameter is multiplied by 1300 to provide the required voltage). The pulse length will be 100 µs. Postoperative assessment of study subjects will be weekly for 4-6 weeks, and monthly thereafter for a total of 12 months. Approximately 8 to 12 weeks following therapy, a biopsy of the tumor site will be performed. Use of CT or MRI scans will be utilized in accordance to standard medical follow-up evaluation of HNC subjects.

Tumor evaluation will include measuring the tumor diameter (in centimeters) and estimating its volume (in cubic centimeters). Prior to intratumoral administration of bleomycin sulfate, the tumor site will be anesthetized with 1% lidocaine (xylocaine) and 1:100,000 epinephrine. The concentration of bleomycin sulfate injected will be 4 units per milliliter, up to a maximum dose of 5 units per tumor. If more than one tumor per subject is treated, a total of 20 units per subject should not be exceeded. The dose of bleomycin administered will be 1 unit/cm$^3$ of calculated tumor volume. Approximately ten minutes subsequent to the injection of bleomycin sulfate, the applicator will be placed on the tumor and electrical pulses initiated. In this study, success will be defined as significant tumor regression in a period of 16 weeks or less without major side effects seen with traditional therapy. There are four possible response outcomes:

Complete Response (CR): Disappearance of all evidence of tumor as determined by physical examination, and/or biopsy.

Partial Response (PR): 50% or greater reduction in tumor volume.

No Response (NR): less than 50% reduction in tumor volume.

If the tumor increases (25% tumor volume) in size, other therapy, if indicated, will be instituted per subject's desire.

Example 7

Low Voltage Long Pulse Length (LVLP) EPT

Electroporation response of MCF-7 will be carried out at both high voltage/short pulse length (HVSP) and low voltage/long pulse length (LVLP) using an XTT assay. XTT is a tetrazolium reagent, 2,3-bis(2-methoxy-4-nitro-5-sulfophenyl)-5-[(phenylamino) carbonyl]-2H-tetrazolium hydroxide, which is metabolically reduced in viable cells to a water-soluble formazan product. Therefore, only the cells which are live convert XTT to formazan. The metabolic conversion of XTT to formazan after 70 hours will be measured spectrophotometrically at 450 nm. (M. W. Roehm, et al., An Improved Colorimetric Assay for Cell Proliferation and Viability Utilizing the Tetrazolium Salt XTT, J. Immunol. Methods 142:2, 257-265, 1991.) The percent cell survival values will be calculated using a formula from the O.D. values of the sample. (Control, with 100% cell survival (D-E) and control with 0% cell survival (D-E with SDS).) The experiments with HVSP will be done to permit direct comparison with the LVLP mode of EPT.

Example 8

Cytotoxicity of Drugs with EPT In Vitro

Cells will be obtained from ATTC (American Type Tissue Collection, Rockville, Md., USA) and maintained by their recommended procedures. The cells will be suspended in appropriate medium and uniformly seeded in 24/96 well plates. One of bleomycin, cisplatin, mitomycin C, doxorubicin and taxol will be added directly to the cell suspensions at final concentrations of about $1 \times 10^{-4}$ (1E-4) to $1.3 \times 10^{-9}$ (1.3E-9). The electrical pulses generated by a BTX T820 ElectroSquarePorator will be delivered to the cell suspensions in microplates using a BTX needle array electrode as described herein. Depending on the experiment, six pulses of either 100 µs or 10 ms and at various nominal electric fields of either high voltage or low voltages will be applied between two opposite pairs of a six-needle array using EPT-196 needle array switch. The microplates will be incubated for either 20 hrs or 70 hrs and the cell survival will be measured by the XTT assay.

Example 9

Unipolar Waveform Prototype

Prototypes will be assembled, e.g., using off-the-shelf instruments. The prototypes will be used to produce two opposing waveforms or signals that create an interference waveform. As illustrated in FIGS. 12a and 12b, in one prototype, each opposing waveform may be unipolar, and, in combination, the resultant interference waveform may also be unipolar as illustrated in FIG. 12c. In other prototypes, each opposing waveform may be bipolar as illustrated in FIG. 11, and the resultant interference waveform may therefore be bipolar.

Although the invention has been described with reference to the presently preferred embodiment, it should be understood that various modifications can be made without departing from the spirit of the invention. Accordingly, the invention is limited only by the following claims.

The invention claimed is:

1. An electroporation device comprising:
    an applicator;
    a plurality of electrodes extending from the applicator, the electrodes being associated with a cover area;
    a power supply in electrical communication with the electrodes, the power supply configured to generate one or more electroporating signals, wherein the power supply is associated with an output power and the electroporating signal is associated with an electric field; and
    a guide member coupled to the electrodes and in operable communication with the power supply, wherein the guide member is configured to adjust the cover area of the electrodes, and wherein the guide member provides feedback to the power supply regarding the cover area of the electrodes; and wherein the output power is adjusted at least partially in response to the feedback from the guide member.

2. The device of claim 1, wherein the guide member is slidably coupled to the applicator.

3. The device of claim 1, wherein the guide member is slidably coupled to the applicator, wherein the applicator is associated with an applicator end, and wherein sliding the guide member toward the applicator end decreases the cover area.

4. The device of claim 1, wherein the guide member is slidably coupled to the applicator, wherein the applicator is associated with an applicator end, and wherein sliding the guide member away from the applicator end increases the cover area.

5. The device of claim 1, wherein at least a portion of the electrodes are positioned within the applicator in a circular arrangement.

6. The device of claim 1, wherein the electric field is maintained substantially within a predetermined range.

7. The device of claim 1, wherein the electric field is maintained to about 1300 V/cm.

8. The device of claim 1, wherein the power supply is configured to reduce the output power in response to a reduced cover area of the electrodes.

9. The device of claim 1, wherein the power supply is configured to increase the output power in response to an increased cover area of the electrodes.

10. The device of claim 1, wherein the power supply is configured to maintain the electric field within a predetermined range so as to prevent damage in the cells within the cover area.

11. The device of claim 1, wherein the power supply is configured to maintain the electrical field within a predetermined range so as to substantially minimize pain.

12. The device of claim 1, wherein the power supply provides a first electrical signal to a first electrode and a second electrical signal to a second electrode, wherein the first and second electrical signals combine to produce a wave having a beat frequency, and wherein the first and second electrical signals each have at least one of a unipolar waveform and a bipolar waveform.

13. The device of claim 12, wherein the first electrical signal has a first frequency and a first amplitude, wherein the second electrical signal has a second frequency and a second amplitude, wherein the first frequency is different from or the same as the second frequency, and wherein the first amplitude is different from or the same as the second amplitude.

14. An electroporation device comprising:
an applicator;
a plurality of electrodes extending from the applicator, the electrodes being associated with a cover area;
a power supply in electrical communication with the electrodes, the power supply configured to generate one or more electroporating signals, wherein the power supply is associated with an output power and the electroporating signal is associated with an electric field;
a guide member coupled to the electrodes and moveable with respect to the applicator to adjust the cover area of the electrodes, wherein the guide member is coupled to a potentiometer, and wherein the potentiometer is configured to adjust the output power in response to movement of the guide member with respect to the applicator.

15. The device of claim 14, wherein the potentiometer is configured to reduce the output power in response to a reduced cover area of the electrodes.

16. The device of claim 14, wherein the potentiometer is configured to increase the output power in response to an increased cover area of the electrodes.

17. The device of claim 14, wherein the potentiometer is configured to maintain the electric field to about 1300 V/cm.

18. The device of claim 14, wherein the power supply provides a first electrical signal to a first electrode and a second electrical signal to a second electrode, wherein the first and second electrical signals combine to produce a wave having a beat frequency, and wherein the first and second electrical signals each have at least one of a unipolar waveform and a bipolar waveform.

19. The device of claim 18, wherein the first electrical signal has a first frequency and a first amplitude, wherein the second electrical signal has a second frequency and a second amplitude, wherein the first frequency is different from or the same as the second frequency, and wherein the first amplitude is different from or the same as the second amplitude.

* * * * *